(12) United States Patent
Masubuchi et al.

(10) Patent No.: US 12,137,928 B2
(45) Date of Patent: Nov. 12, 2024

(54) METHOD AND SYSTEM FOR CONTROLLING ROTATIONAL SPEED OF AN AGITATOR OR CATHETER

(71) Applicant: TERUMO KABUSHIKI KAISHA, Tokyo (JP)

(72) Inventors: Yuki Masubuchi, Hiratsuka (JP); Steve Woodard, Newark, CA (US); Mansour Saleki, Newark, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 542 days.

(21) Appl. No.: 17/474,719

(22) Filed: Sep. 14, 2021

(65) Prior Publication Data
US 2021/0401448 A1  Dec. 30, 2021

Related U.S. Application Data

(63) Continuation of application No. PCT/JP2020/010878, filed on Mar. 12, 2020, which is a continuation-in-part of application No. 16/354,687, filed on Mar. 15, 2019.

(51) Int. Cl.
*A61B 17/32* (2006.01)
*A61B 90/00* (2016.01)

(52) U.S. Cl.
CPC ........ *A61B 17/32002* (2013.01); *A61B 90/03* (2016.02); *A61B 2090/031* (2016.02)

(58) Field of Classification Search
CPC .............. A61B 17/32002; A61B 90/03; A61B 2090/031; A61B 2017/00017; A61B 17/320758
See application file for complete search history.

(56) References Cited

U.S. PATENT DOCUMENTS

| | | | |
|---|---|---|---|
| 4,705,038 A | 11/1987 | Sjostrom et al. | |
| 6,024,751 A | 2/2000 | Lovato et al. | |
| 6,451,036 B1 * | 9/2002 | Heitzmann | A61B 17/320758 |
| | | | 606/159 |
| 7,713,231 B2 | 5/2010 | Wulfman et al. | |
| 8,388,582 B2 | 3/2013 | Eubanks et al. | |

(Continued)

FOREIGN PATENT DOCUMENTS

| | | |
|---|---|---|
| WO | 2011106053 A1 | 9/2011 |
| WO | 2015/109176 A1 | 7/2015 |

OTHER PUBLICATIONS

International Search Report (PCT/ISA/210) and Written Opinion (PCT/ISA/237) mailed on Jun. 23, 2020, by the Japanese Patent Office as the International Searching Authority for International Application No. PCT/JP2020/010878.

(Continued)

*Primary Examiner* — Julian W Woo
(74) *Attorney, Agent, or Firm* — Buchanan Ingersoll & Rooney PC

(57) ABSTRACT

A method and device handle having a slide assembly are disclosed for controlling rotational speed of a catheter assembly under various rotational loads. The method includes setting a first current limit in a processor, activating the catheter assembly to rotate, calculating a current value in rotational period of a first current limit, updating a second current limit from the first current limit, and wherein the second current limit is lower than the first current limit.

20 Claims, 22 Drawing Sheets

(56) References Cited

U.S. PATENT DOCUMENTS

| | | | |
|---|---|---|---|
| 10,052,122 | B2 | 8/2018 | Higgins et al. |
| 10,893,882 | B2 | 1/2021 | Spangler et al. |
| 11,627,982 | B2 * | 4/2023 | Masubuchi .... A61B 17/320758 606/159 |
| 11,819,238 | B2 * | 11/2023 | Farago ............ A61B 17/320758 |
| 11,864,789 | B2 * | 1/2024 | Lee .................. A61B 17/32002 |
| 2001/0004700 | A1 | 6/2001 | Honeycutt et al. |
| 2013/0253552 | A1 * | 9/2013 | Schoenle ....... A61B 17/320758 606/159 |
| 2016/0120565 | A1 | 5/2016 | Kobayashi et al. |
| 2017/0348019 | A1 | 12/2017 | Nakano et al. |
| 2020/0289148 | A1 | 9/2020 | Masubuchi et al. |
| 2020/0289150 | A1 | 9/2020 | Masubuchi et al. |
| 2022/0039824 | A1 | 2/2022 | Masubuchi et al. |

OTHER PUBLICATIONS

U.S. Appl. No. 16/354,687, filed Mar. 15, 2019, entitled "Method and System for Controlling Rotational Speed of an Agitator or Catheter", published as U.S. Application Publication No. 2020/0289150, naming Yuki Masubuchi, et al. as inventors.

U.S. Appl. No. 16/354,795, filed Mar. 15, 2019, entitled "Method and System for Controlling Rotational Speed of an Agitator or Catheter", published as U.S. Application Publication No. 2020/0289148, naming Yuki Masubuchi, et al. as inventors.

U.S. Appl. No. 17/451,885, filed Oct. 22, 2021, entitled "Method and System for Controlling Rotational Speed of an Agitator or Catheter", published as U.S. Application Publication No. 2022/0039824, naming Yuki Masubuchi, et al. as inventors.

International Search Report (Form PCT/ISA/210) and the Written Opinion of the International Searching Authority (Form PCT/ISA/237) issued May 27, 2021, by the European Patent Office in corresponding International Application No. PCT/JP2020/010877. (11 pages).

* cited by examiner

METHOD AND SYSTEM FOR CONTROLLING ROTATIONAL SPEED OF AN AGITATOR OR CATHETER

CROSS-REFERENCES TO RELATED APPLICATIONS

This application is a continuation of International Patent Application No. PCT/JP2020/010878 filed on Mar. 12, 2020, which claims priority to U.S. patent application Ser. No. 16/354,687 filed on Mar. 15, 2019, the entire content of both of which is incorporated herein by reference.

FIELD OF THE INVENTION

The present disclosure generally relates to a method and system for controlling rotational speed of an agitator or catheter and more specifically to a method and system for controlling rotational speed for an agitator or catheter in a device handle of a medical device for cutting a substance from an inner wall surface of a body lumen.

BACKGROUND DISCUSSION

A thrombus, or blood clot, occurs in the vascular system as a result of blood coagulation from injury or turbulent blood flow. Due to its ability to restrict blood flow, if a thrombus is generated in a vascular lumen, it should be removed. Deep vein thrombosis involves formation of a thrombus in a vein existing in a deep part of the body such as a femoral vein or a popliteal vein. One danger of the presence of deep vein thrombosis (DVT) is that thrombi can dislodge and embolize resulting in compromised pulmonary function.

Several methods have been developed to treat deep vein thrombosis. One method is known in which a shaft main body of a catheter system is inserted into a blood vessel, and then an agent such as a thrombolytic agent is injected into an embolus portion to dissolve and remove the thrombus. However, this technology to remove thrombi is known to cause bleeding. In addition, in coronary arteries a percutaneous transluminal coronary angioplasty (PTCA) may be performed to open arteries affected by plaque or thrombus formation. In this method, the blood vessel is dilated using a balloon, and a mesh-shaped or coil-shaped stent is left to indwell the blood vessel as a support for the blood vessel. However, these methods are less likely to be applied when the plaque of the stenosed site becomes calcified or if the stenosed site develops in a bifurcated portion of the coronary arteries.

A treatment has been proposed in which a thrombus is mechanically broken and is suctioned out of the vascular lumen. The thrombus is subsequently removed by a shaft main body inserted in a blood vessel. With this treatment, it is possible to reduce or potentially eliminate the use of the agent entirely. Such a system is disclosed in U.S. Pat. No. 6,024,751.

SUMMARY

A method and system are disclosed to ensure proper removal of a stenosed site within a blood vessel and reduce the hazard on biological tissues and/or blood vessels by stopping the rotation of an agitator or catheter assembly upon engagement with the biological tissues and/or blood vessels.

A method is disclosed for controlling rotational speed of a catheter assembly under various rotational loads, the method comprising: setting a first current limit in a processor; activating the catheter assembly to rotate; calculating a current value in a rotational period of a first current limit; updating a second current limit from the first current limit; and wherein the second current limit is lower than the first current limit.

A method is disclosed of limiting torque of a catheter assembly with a rotational profile, the method comprising: setting a starting value for a current limit of a motor, the motor being configured to drive the catheter assembly; calculating a motor current of the motor during a driving of the catheter assembly in a first direction; and updating the current limit of the motor as a function of the current limit based on the calculated motor current.

A device handle is disclosed for cutting substances inside a body lumen, the device handle comprising: a slide assembly, the slide assembly including a drive shaft assembly configured to rotate a catheter assembly, a motor configured to impart a rotational force to the drive shaft assembly and the catheter assembly, and a processor, wherein the processor is configured to: drive the catheter assembly so that the catheter assembly attains at a target rotational speed in a first direction; update a second current limit in the first direction from a first current limit in the first direction, and wherein the second current limit in the first direction is lower than the first current limit in the first direction; if a rotational speed in the first direction was not achieved at the target rotational speed, setting a first current limit in the second direction that is higher than the first current limit in the first direction when driving the catheter assembly so that the catheter assembly attains at the target rotational speed in a second direction; and alternate the driving of the catheter assembly between the first direction and the second direction.

A method is disclosed for controlling rotational speed of a catheter assembly under various rotational loads, the method comprising: driving the catheter assembly at a target rotational speed in a first direction pursuant to a rotational speed profile; driving the catheter assembly at the target rotational speed in a second direction pursuant to the rotational speed profile; and alternating the driving of the catheter assembly between the first direction and the second direction.

A method is disclosed of limiting torque of a catheter assembly with a rotational profile, the method comprising: setting a starting value for a current limit a motor, the motor being configured to drive the catheter assembly; measuring a motor current of the motor during a driving of the catheter assembly in a first direction; and updating the current limit of the motor as a function of the current limit based on the measured motor current.

A device handle is disclosed for cutting substances inside a body lumen, the device handle comprising: a slide assembly, the slide assembly including a drive shaft assembly configured to rotate a catheter assembly, a motor configured to impart a rotational force to the drive shaft assembly and the catheter assembly, and a processor, wherein the processor is configured to: drive the catheter assembly at a target rotational speed in a first direction pursuant to rotational speed profile; drive the catheter assembly at the target rotational speed in a second direction pursuant to the rotational speed profile; and alternate the driving of the catheter assembly between the first direction and the second direction.

DETAILED DESCRIPTION

Figure 1A:
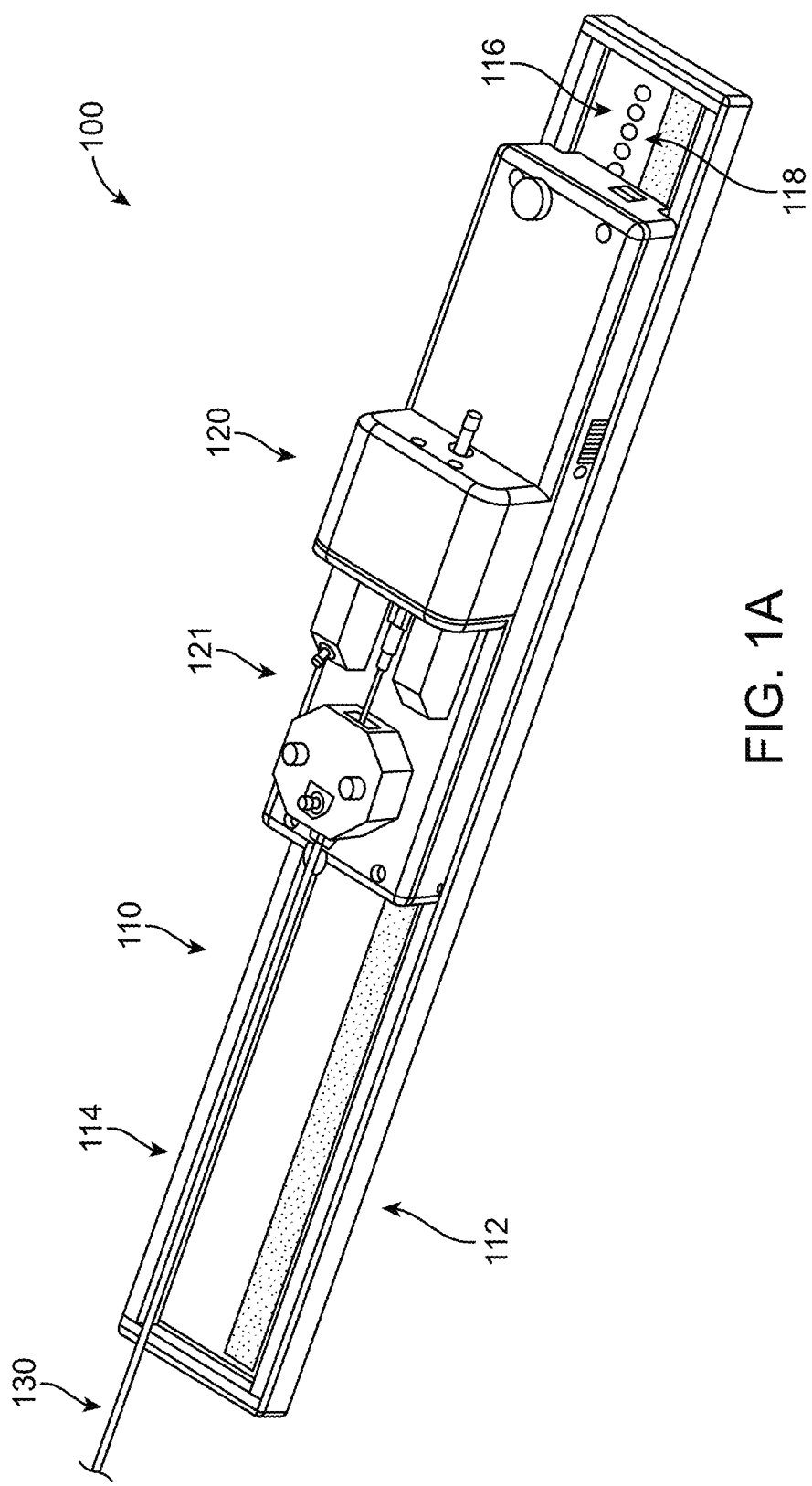
FIG. 1A is a perspective view of a handle with a slide assembly for use with an agitator or catheter in accordance with an exemplary embodiment.

Hereinafter, embodiments of the present disclosure will be described with reference to the drawings. In order to facilitate description, dimensional ratios in the drawings are exaggerated and thus are different from actual ratios in some cases.

FIG. 1A is a perspective view of a medical device 100, which includes a handle 110 having a slide assembly 120 for use with a catheter assembly 130 in accordance with an exemplary embodiment. As shown in FIG. 1A, the medical device 100 can be used for therapy (treatment) to cut a stenosed site or an occluded site which is caused by plaque, thrombus or the like inside the blood vessel (not shown). In this description, a side of the device 100, which is inserted into the blood vessel is referred to as a "distal side", and an operating hand side is referred to as a "proximal side".

As shown in FIG. 1A, the handle 110 includes a guide rail assembly 112 having one or more tracks 114 configured to receive the slide assembly 120. The catheter assembly 130 is configured to be attached or received on a distal portion 121 of the slide assembly 120. In accordance with an exemplary embodiment, the slide assembly 120 can include a plurality of bearings, for example, ball bearing configured to run on a track 114 for smoother operation. For example, in accordance with an exemplary embodiment, the plurality of bearings can be four (4) 10 mm ball bearings.

In accordance with an exemplary embodiment, the medical device 100 is preferably configured to have, for example, a manual pull back of approximately 250 mm to 350 mm, and preferably at least 300 mm. For example, on an inner surface 116 of the handle 110, a plurality of markings or indicia 118 can be placed to help an operator determine an amount of axial displacement of the agitator of the catheter assembly 130 during use. In accordance with an exemplary embodiment, the pull back is a manual control pull back only. As shown in FIG. 1A, the handle 110 can include a plurality of cover plates, for example, a top front cover plate and a back cover plate. In accordance with an exemplary design, for example, the handle 110 can have a height of approximately 75 mm to 90 mm, a width of approximately 80 mm to 100 mm, and a length of approximately 300 mm to 400 mm.

In accordance with an exemplary embodiment, the handle 110 is preferably designed to detect and stop, for example, an agitator 132, which is part of the catheter assembly 130, when the agitator 132 engages a blood vessel wall. For example, in accordance with an exemplary embodiment, a control system, for example, a processor or controller within the slide assembly 120 of the handle 110 can be configured to have a vessel detection condition, which can detect with 180 degrees of vessel twisting, and wherein the 180 degrees of vessel twisting is equal to 180 degrees plus 90 degrees at Luer connection to the catheter assembly (or catheter) 130. In accordance with an exemplary embodiment, the handle 110 is configured that after detection of, for example, vessel twisting, the luer connection 210 to the catheter assembly 130 stops within 360 degrees.

Figure 1B:
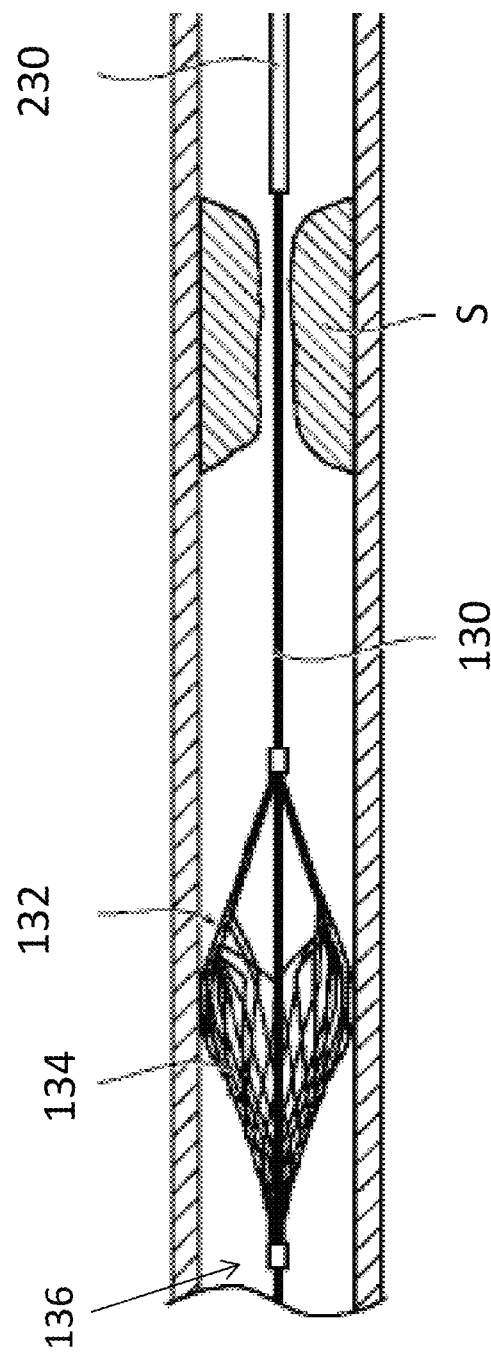
FIG. 1B is a cross-sectional view illustrating an agitator on a distal end of a catheter assembly in a blood vessel having a stenosed site in accordance with an exemplary embodiment.

As illustrated in FIG. 1B, the catheter assembly 130 of the medical device 100 can include an agitator 132. In accordance with an exemplary embodiment, the agitator 132 can be arranged or located on a distal end or distal portion of the catheter assembly 130. The agitator 132 can be, for example, a cutting unit, which is expandable and contractible radially outward. For example, the agitator 132 can be a mechanical agitator along the treatment length of the catheter assembly 130 for mechanically agitating a clot at the treatment site and/or for dispersing lytic at the treatment site. The mechanical agitator may comprise a radially expansible agitator 132 that is rotatable and/or axially translatable with the catheter assembly 130. In accordance with an exemplary embodiment, the radially expansible agitator 132 the catheter assembly 130 may be self-expanding, for example, a Nitinol (Ni—Ti) cage 134. In accordance with an exemplary embodiment, the radially expansible agitator has a mass 136 on a distal end providing rotational inertia. For example, as shown in in FIG. 1B, the mass 136 can be produced from a collection of the distal ends of the material constituting the radially expansible agitator 132, for example, the Nitinol. In accordance with an exemplary embodiment, the agitator 132 can have a helical shape and be configured to dilate and contract when accelerated and decelerated, respectively, due to the rotational inertia and the helical design.

In accordance with an exemplary embodiment, for example, as a configuration material of the agitator 132, a shape memory alloy, which is provided with a shape memory effect or super-elasticity by means of heat treatment, or stainless steel, can be preferably used. As the shape memory alloy, Ni—Ti-based alloys, Cu—Al—Ni-based alloys, Cu—Zn—Al-based alloys, and combinations of the shape memory alloys, are preferably used.

In accordance with an exemplary embodiment, for example, the agitator 132 of the catheter assembly 130 may comprise a resilient element that may be radially constrained to have a low profile (small diameter) and may be freed from radial constraint to have an enlarged profile (large diameter) with a non-linear geometry. Radial constraint may be provided by a sleeve or sheath that may be axially advanced and retracted relative to the catheter assembly 130 to cover and uncover the radially expansible agitator. In this way, the catheter assembly 130 may be introduced to a treatment site within the vasculature with the expansible agitator 132 covered (and thus radially constrained). After the desired treatment site S is reached, an outer sheath 230 (FIG. 7) may be axially retracted to release the radially expansible agitator 132 so that it expands to engage the clot in the blood vessel. The agitator 132 may then be rotated and/or axially translated to engage and disrupt the clot in combination with the release, for example, of a thrombolytic agent.

Figure 2:
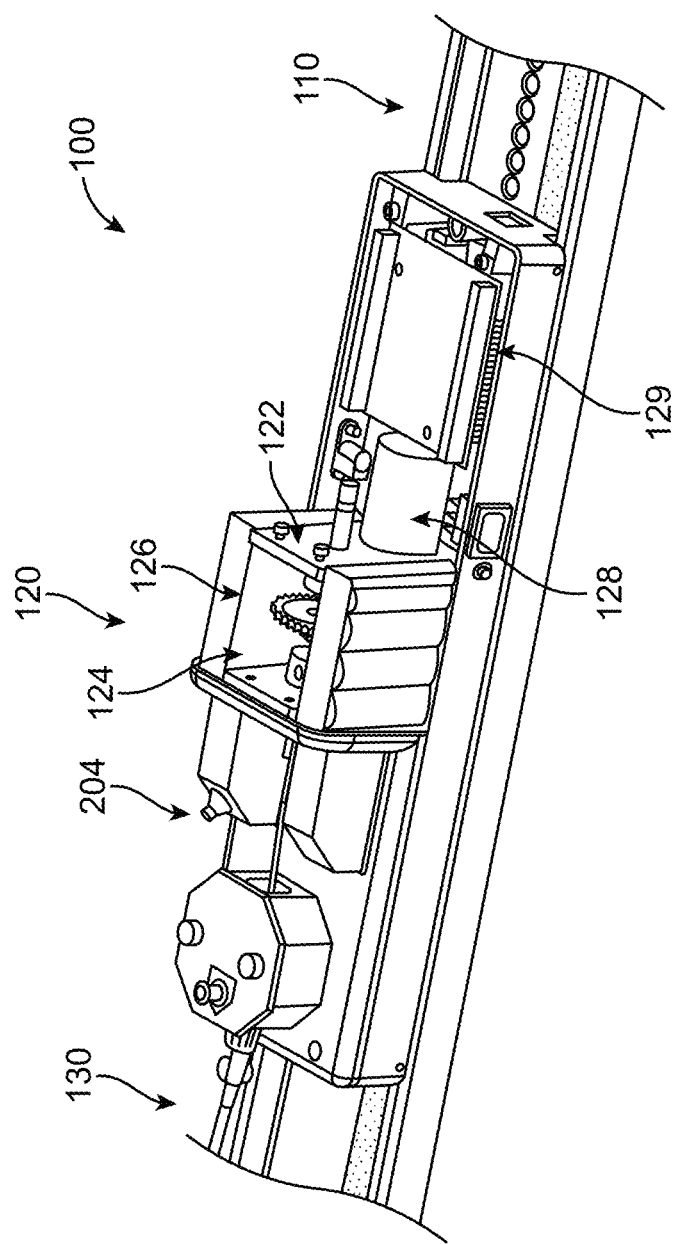
FIG. 2 is another perspective view of the handle with the slide assembly for use with the agitator or catheter in accordance with an exemplary embodiment.

FIG. 2 is another perspective view of the handle 110 with the slide assembly 120 for use with the agitator or catheter in accordance with an exemplary embodiment. As shown in FIG. 2, the slide assembly 120 can include a drive module frame 122 configured to receive a drive shaft assembly 124. The drive shaft assembly 124 can include, for example, a drive shaft with a press fit gear and code wheel attachments 126. In accordance with an exemplary embodiment, for example, an extended motor shaft can be used to eliminate the need for a separate driving shaft. The slide assembly 120 also includes a motor 128. The drive shaft assembly 124 can include a drive gear, which meshes with the driven gear (or rotary shaft) of the motor 128. The motor 128 can serve as a drive source including the rotary shaft to which the drive gear is fixed.

In accordance with an exemplary embodiment, the motor 128 can be configured to have an operating voltage, for example, of approximately 6 to 12 V (volts). For example, in accordance with an exemplary embodiment, the motor can be rated for 4.5 V to 15 V, having a high torque constant, for example, around 6.5 mNm/A to 7.0 mNm/A, a speed constant of approximately, 1350 RPM/V to 1400 RPM/V, and a max power of 40 W at 12 V.

In accordance with an exemplary embodiment, the slide assembly 120 also includes a plurality of electronic components 129, which can be mounted, for example, on a printed circuit board (PCB)(not shown). The electronic components 129 are configured to carry out the processes as disclosed herein. The electronic components 129 can include, for example, a processor or a microprocessor, an operating system, one or more memories or memory cards, and/or a servo motor controller. In accordance with an exemplary embodiment, the processor has at least one from an instruction unit that instructs the motor controller and a calculating unit that calculates the current for example, the average current that monitored about 50 times per 1 mm second. The motor controller has at least one from a current supply unit to the motor, a decision unit that decide amount of the current to flow, a monitoring unit to monitor a flowing current or a current to be flowed. The processor may decide amount of the current to flow. In accordance with an exemplary embodiment, the handle 110 of the medical device 100 can include, for example, a power jack, a USB port, a power switch and status LED, and an activate switch 204 for the agitator 132.

For example, in accordance with an exemplary embodiment, the mechanical drive of the drive shaft assembly 124 can include an encoder and code wheel, which is configured to convert a reading from the code wheel into a speed reading. For example, the encoder can be a three (3) channel optical encoder, which uses, for example, a 500 counter per revolution (CPR) quadrature signal for motor control. In accordance with an exemplary embodiment, an index signal is sent to the processor to track total revolutions. In accordance with an exemplary embodiment, rather than an encoder and code wheel, a speed sensor could be used.

In accordance with an exemplary embodiment, the drive shaft assembly 124 can be configured to have an agitator 132 having a rotation speed of between approximately 1100 RPM (revolutions per minute) to 12000 RPM, and having a rotational direction in each of a first direction and a second direction (i.e., clockwise and counterclockwise) s at the target agitator speed from four (4) revolutions to sixteen (16) revolutions depending on vessel patency. For example, when a clot (i.e., blood clot) completely closes the blood vessel and blood flow stops, the vessel patency (i.e., openness of blood vessel) is 0%. When the blood flows in a healthy situation, the blood vessel patency is 100%. In accordance with an exemplary embodiment, vessel patency of 50% to 100% can be acceptable as a successful execution of a treatment in a medical guideline or procedure. For example, in accordance with an exemplary embodiment, the rotating speed of the agitator 132 can obtain the following patency: 1100 RPM, 40% patency; 1600 RPM, 50% patency; 3200 RPM, 100% patency; 10000 RPM, 100% patency; 12000 RPM, 100% patency (trauma).

In accordance with an exemplary embodiment, for example, the drive shaft assembly 124 is preferably configured, for example, to have a peak agitator speed or target of approximately 3200 RPM (revolutions per minute), a maximum speed of approximately 4000 RPM, and a speed of approximately 3 revolutions of the agitator of the catheter assembly 130 at approximately 2000 RPM, for 8 revolutions.

In accordance with an exemplary embodiment, the slide assembly 120 can be programmed to rotate the agitator of the catheter assembly in a manner, which includes eight (8) clockwise revolutions, a rest period of, for example, 500 milliseconds (msec), and eight (8) counter-clockwise revolutions. In accordance with an exemplary embodiment, the process repeats after a 500 msec rest period. In accordance with an exemplary embodiment, the slide assembly 120 can be programmed or configured such that the rotation of the agitator of the catheter assembly includes eight (8) clockwise revolutions (first direction), a coast period (or coast time) in which the agitator or the catheter assembly is not under a rotational load (for example, 3 to 6 revolutions, and more preferably 4 to 5 revolutions), a rest period of, for example, 500 milliseconds (msec), and 8 (eight) counter-clockwise revolutions (second direction). In accordance with an exemplary embodiment, the process repeats after another coast period (coast time), for example, 3 to 6 revolutions, more preferably 4 to 5 revolutions, and a 500 msec rest period. In accordance with an exemplary embodiment, for example, the coast period and the rest period can be 0.4 seconds to 0.6 seconds, and more preferably, are about 0.5 seconds.

Figure 3:
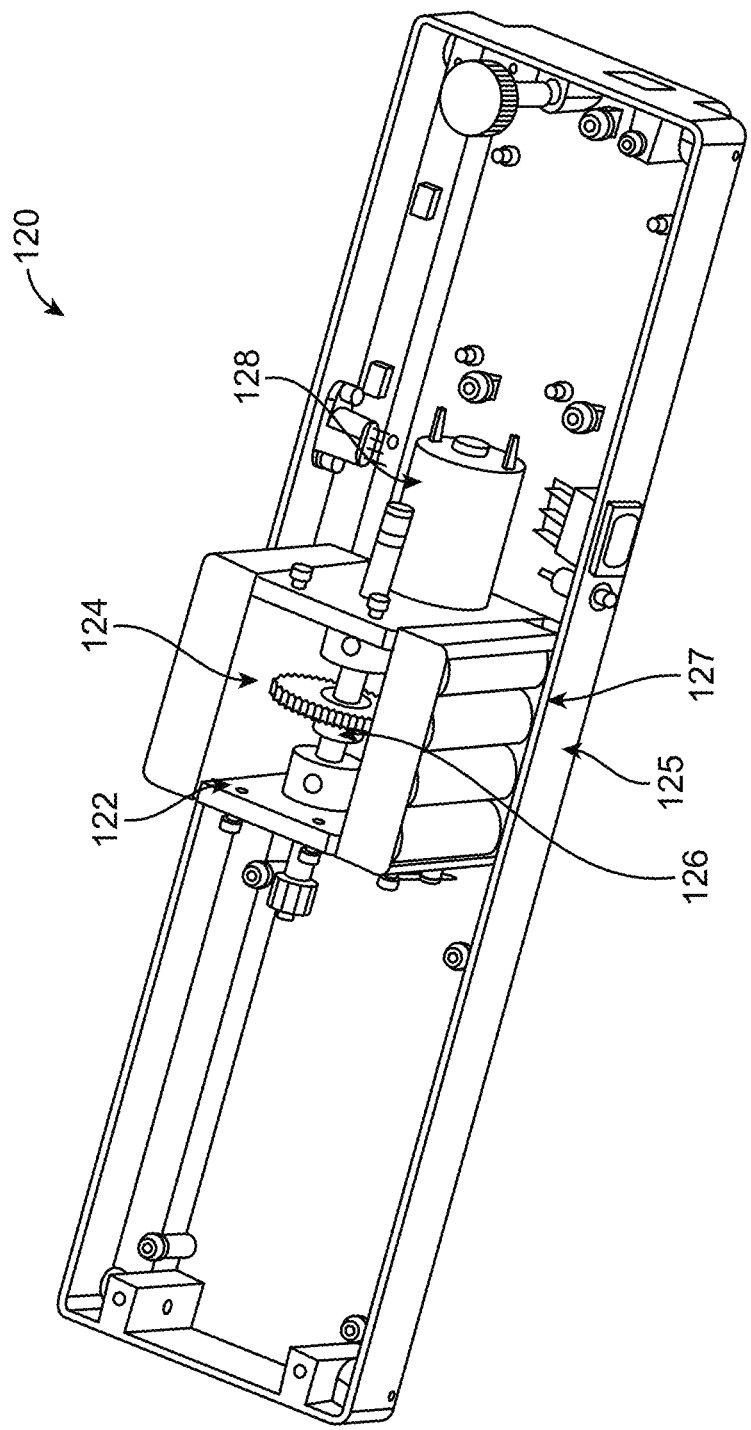
FIG. 3 is a perspective view of the handle and the slide assembly in accordance with an exemplary embodiment.

FIG. 3 is a perspective view of the slide assembly 120 of the handle 110 and a drive module assembly 124 in accordance with an exemplary embodiment. As shown in FIG. 3, the handle 120 can also include a power supply 125, for example, one or more batteries 127. In accordance with an exemplary embodiment, the one or more batteries 127 preferably have a battery life of at least 2.0 hours or more of motor operation. In addition, or alternatively, the slide assembly 120 can include an AC/DC source.

Figure 4:
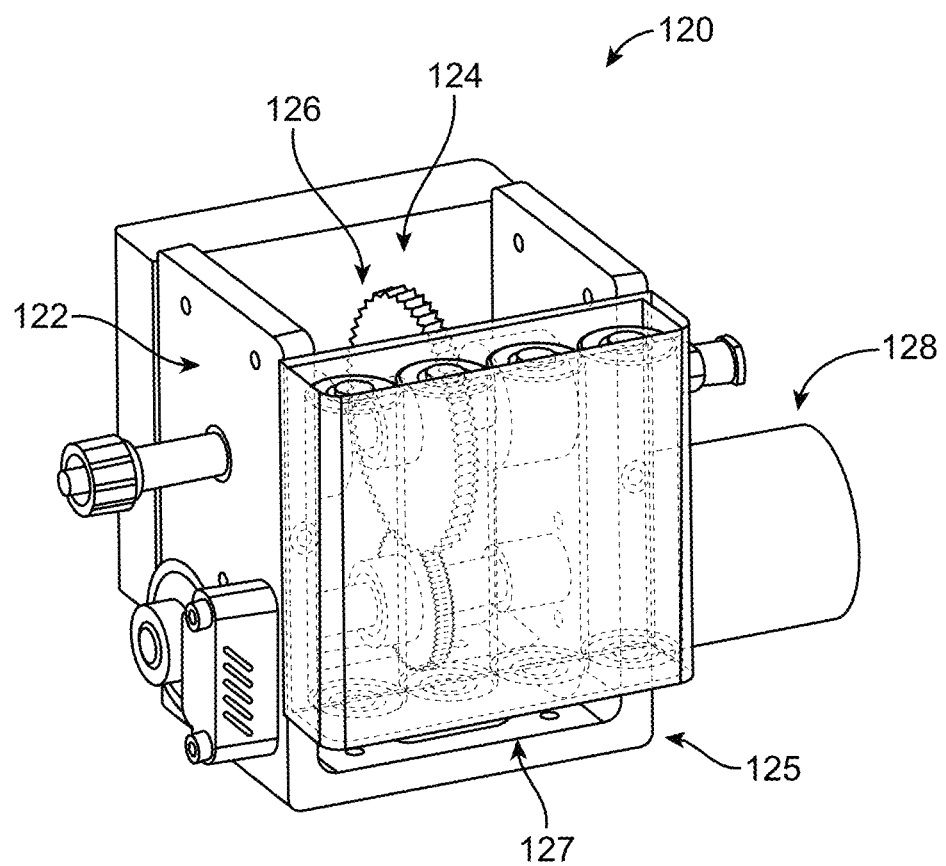
FIG. 4 is a perspective view of a portion of the slide assembly in accordance with an exemplary embodiment.

FIG. 4 is a perspective view of a portion of the slide assembly 120 in accordance with an exemplary embodiment. As shown in FIG. 4, the slide assembly 120 can include the drive module frame 122 configured to receive the drive shaft assembly 124. The drive shaft assembly 124 can include, for example, a stainless steel shaft with a press fit gear and code wheel attachments 126. In addition, in accordance with an exemplary embodiment, one or more batteries 127 can be provided as a power source 125.

Figure 6:
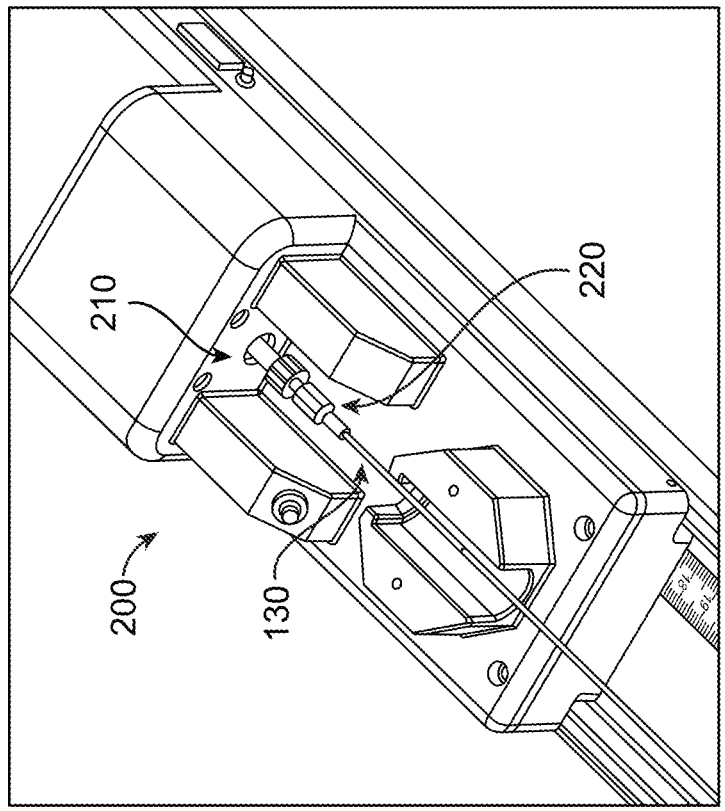
FIG. 6 is a perspective view of the catheter interface on the handle with the agitator shaft luer attached to the handle.
Figure 5:
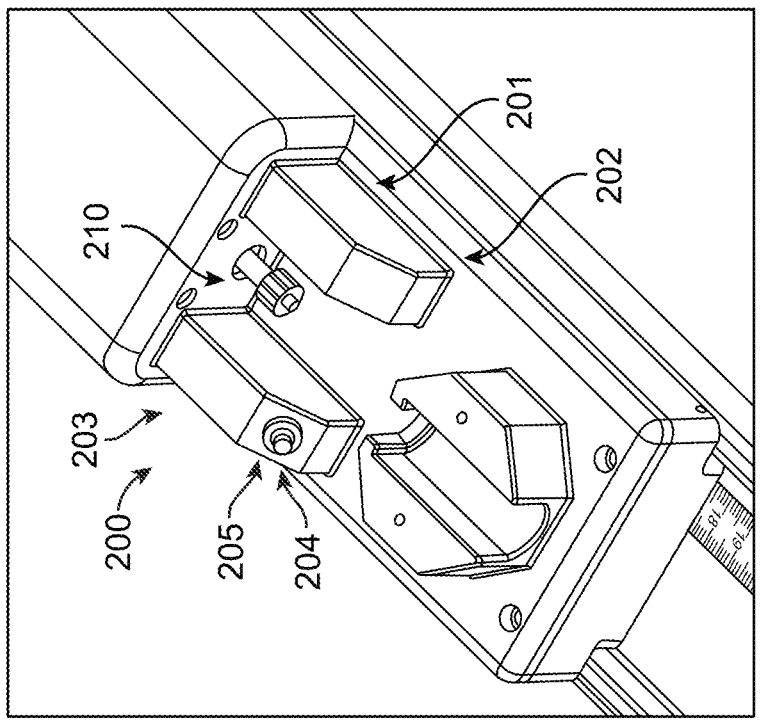
FIG. 5 is a perspective view of a catheter interface on the handle in a ready position without an agitator.

FIGS. 5 and 6 are perspective views of a catheter interface 200 on the handle 110 in a ready position without an agitator, and with an agitator shaft luer 210 attached to a distal end of the drive shaft assembly 124, respectively. As shown in FIGS. 5 and 6, the catheter interface 200 can include a connector 210, for example, a male fitting on a distal end of the drive shaft assembly 124 and which is configured to receive a connector 220, for example, a female connection or shaft luer (or luer lock interface) on a proximal end of the catheter assembly 130.

In accordance with an exemplary embodiment, as shown in FIGS. 5 and 6, the slide assembly 120 of the handle 110 can include a grip feature 202 having a width, for example, of about 65 mm to 75 mm, for example, 70 mm, and arranged to have a right handed thumb located at position 1 201, the middle finger of the right hand at position 2 203, and the index finger of the right hand at position 3 205, which can push the activation switch 204, which activates the rotation of the agitator 132. As shown, the handle 120 is designed to be operated by a user's right hand. In accordance with an alternative embodiment, the position of the activation switch 204, for example, can be moved to an opposite side, such that the slide assembly 120 of the handle 110 can be operated by a user's left hand.

Figure 7:
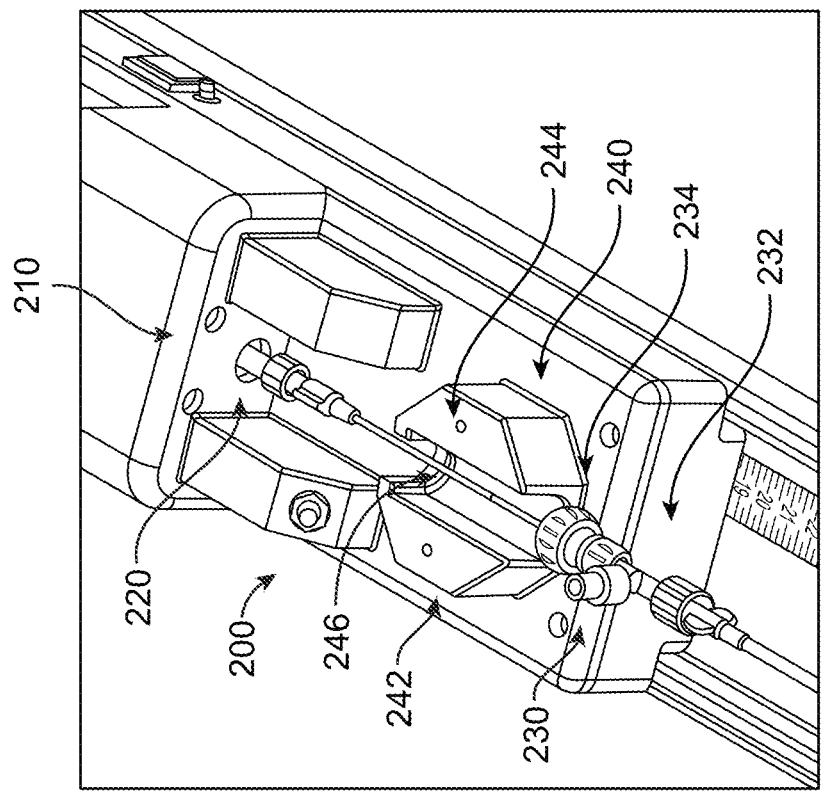
FIG. 7 is a perspective view of the catheter interface on the handle with an agitator module inserted an outer sheath, and the agitator is positioned on a distal end (or position) of a blood clot.

FIG. 7 is a perspective view of the catheter interface 200 on the handle with the catheter assembly 130 and the agitator (or agitator module) (not shown) inserted an outer sheath 230 the agitator is positioned on a distal end (or distal position) of a blood clot. As shown in FIG. 7, the agitator of the catheter assembly 130 is inserted into the outer sheath 230 and positioned on the distal end or side of the blood clot. A configuration material of the catheter assembly 130 and the outer sheath 230 is not particularly limited. However, for example, polyolefin such as polyethylene, polypropylene and the like, polyamide, polyester such as polyethylene terephthalate or the like, fluorine-based polymer such as ETFE and the like, polyether ether ketone (PEEK), or polyimide, can be preferably used for the catheter assembly 130 and the outer sheath 230. In addition, the catheter assembly 130 and the outer sheath 230 may be configured to include multiple materials, or a reinforcing material such as a wire may be incorporated therein.

In accordance with an exemplary embodiment, as shown in FIG. 7, the catheter interface 200 also includes a receiving area 240 configured to receive a luer (or tee connection) 232 on a proximal end 234 of the outer sheath 230. As shown in FIG. 7, the receiving area 240 can have a pair of side walls 242, 244, and rounded or oval shaped receiving portion 246.

Figure 8:
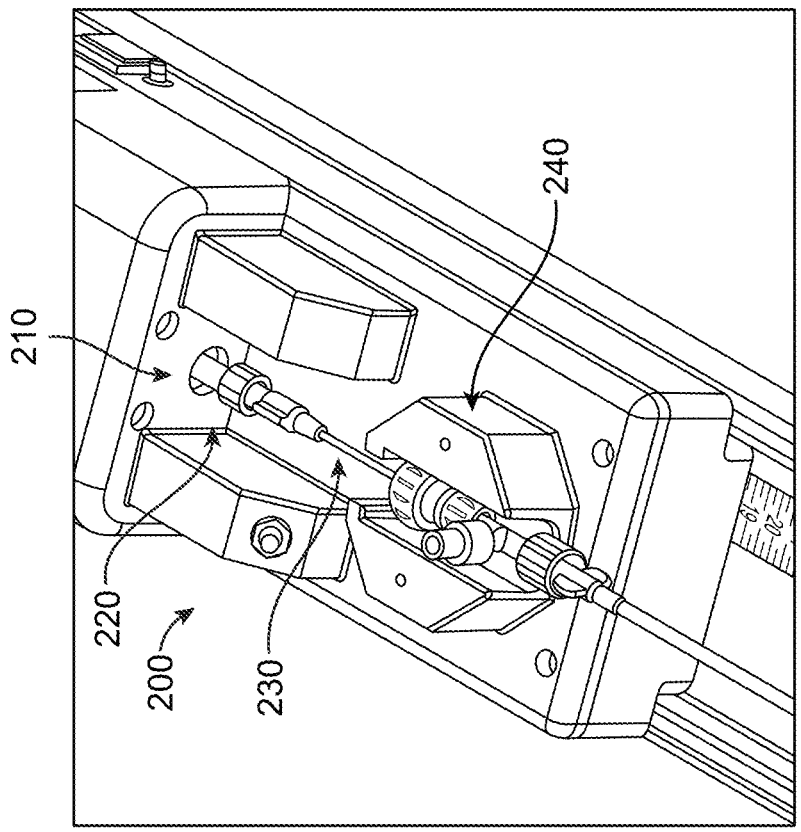
FIG. 8 is a perspective view of the catheter interface on the handle and wherein the outer sheath has pull back to deploy agitator.

FIG. 8 is a perspective view of the catheter interface 200 on the handle and wherein the tee connection 232 of the outer sheath 230 is pull backed to deploy the agitator (not shown) of the catheter assembly 130. As shown in FIG. 8, the agitator of the catheter assembly 130 can be deployed on the distal end or side of the blood clot at which time, the luer (or tee assembly) 232 on the proximal end 234 of the outer sheath 230 can be moved proximally and placed within the receiving area 240.

Figure 9:
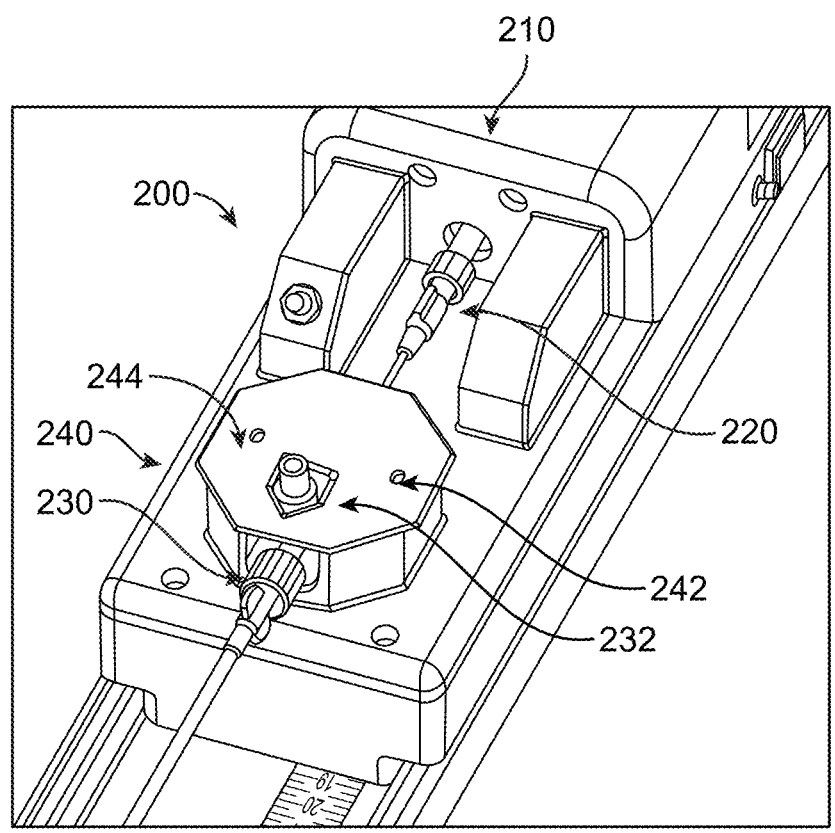
FIG. 9 is a perspective view of the catheter interface on the handle after the clamping plate has been installed over a luer.

FIG. 9 is a perspective view of the catheter interface 200 on the slide assembly 120 of the handle 110 after a clamping plate 242 has been installed over the luer (or tee) 232. As shown in FIG. 9, the clamping plate 242 can include a recess 244, which helps secure the luer (or tee) 232 within the receiving area 240. In accordance with an exemplary embodiment, the luer (or tee) 232 can be a tissue plasminogen activator (TPA) luer or tee 232.

Figure 10:
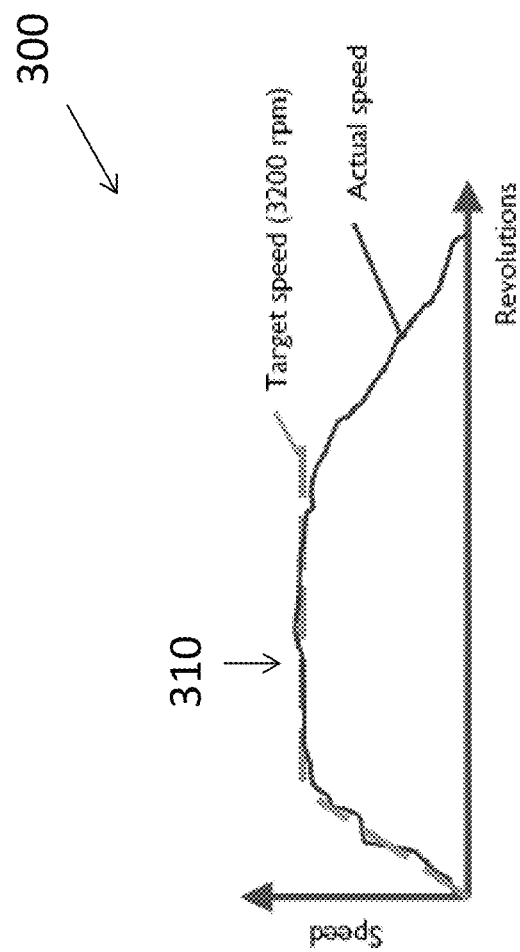
FIG. 10 is rotational speed profile illustrating speed versus revolutions in accordance with an exemplary embodiment.

FIG. 10 is rotational speed profile 300 illustrating speed versus revolutions in accordance with an exemplary embodiment. As shown in FIG. 10, in accordance with an exemplary embodiment, during use of the handle 110 and the sliding assembly 120 to remove a blood clot, the speed 310 of the agitator of the catheter assembly 130 gradually increases to a target agitator speed of, for example, approximately 3200 RPM, and then decreases. As shown in FIG. 10, for a predetermine number of revolutions, for example, 8 revolutions, in the first or second direction as disclosed herein at a target rotational speed, a portion of the 8 revolutions, i.e. at initial startup will be performed at less the target rotational speed of 3200 RPM.

Figure 11:
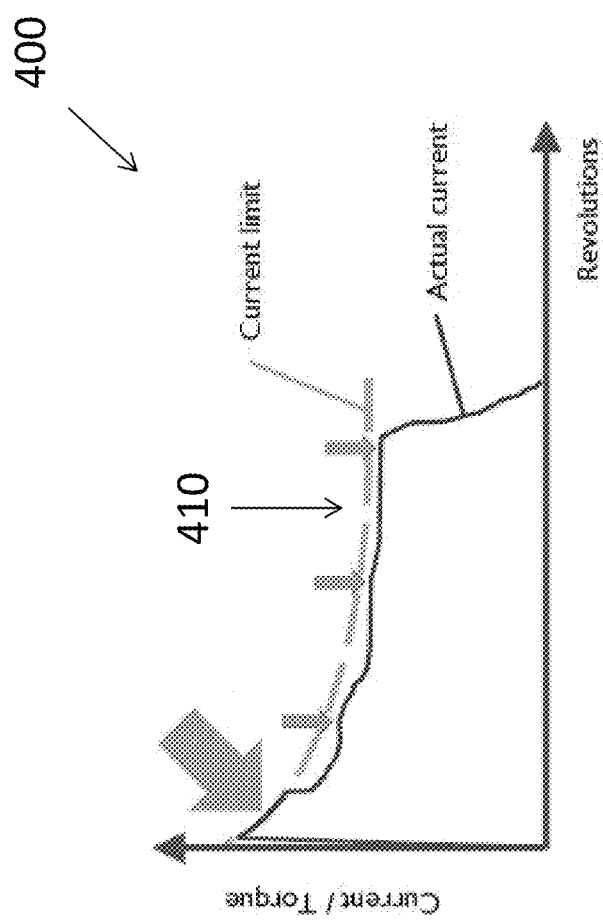
FIG. 11 is a rotational speed profile illustrating current/torque versus revolutions in accordance with an exemplary embodiment.

FIG. 11 is a rotational speed profile 400 illustrating current/torque versus revolutions in accordance with an exemplary embodiment. As shown in FIG. 11, and in accordance with an exemplary embodiment, the drive motor 128 can be controlled by the electronic components 129, for example, a processor, a microprocessor, or controller, such that the drive motor 128 follows the speed profile as shown in FIG. 10, however, the circuitry 129 does not allow the current to exceed a predetermined or predefined limit 410 as shown in FIG. 11. As shown in FIG. 11, after an initial peak, the current is only allowed to drop below the current limit 410, or stays the same. Thus, by limiting the torque, an operator of the medical device 100 can detect and stop the agitator 132 when the medical device 100 engages the blood vessel wall.

For example, in accordance with an exemplary embodiment, the device handle 100 can be configured to control a rotational speed of a catheter assembly 130, for example, an agitator 132 under various rotational loads. As set forth above, the device handle 110 can include the slide assembly 120 having a drive shaft assembly 124 configured to rotate the catheter assembly 130, the motor 128 configured to impart a rotational force to the drive shaft assembly 124 and the catheter assembly 130, and a processor, which carries out the process of driving a catheter assembly 130 at a target rotational speed in a first direction (for example, clockwise), and stopping the rotational direction when a predetermined torque limitation is exceeded.

In accordance with an exemplary embodiment, the processor can be configured to carry out a process of further changing the rotational direction of the catheter assembly 130 from the first direction to a second direction (for example, counterclockwise), monitoring the rotational speed of the catheter assembly 130, and updating the predetermined torque limitation to achieve the target rotational speed for the rotational direction of the catheter assembly 130 in a same direction as the rotational speed of the catheter assembly 130 obtained during the monitoring of the rotational speed. In accordance with an exemplary embodiment, if the rotational speed is less than the target rotational speed, the processor can increase an initial current (or starting current) for a next cycle of the rotational direction of the catheter assembly 130.

In accordance with an exemplary embodiment, the changing of the rotational direction of the catheter assembly 130 can include reducing the torque applied to the catheter assembly 130 to zero after a predetermined number of rotations in the first direction, allowing the catheter assembly to come to a stop, and stopping the rotation of the catheter assembly 130 for a predetermined time before rotating the catheter assembly 130 in the second direction. In addition, the process can include rotating the catheter assembly in the second direction for the predetermined number of rotations in the second direction, reducing the torque applied to the catheter assembly to zero after the predetermined number of rotations in the second direction, allowing the catheter assembly to come to a stop, and stopping the rotation of the catheter assembly for the predetermined time before rotating the catheter assembly in the first direction. The rotation of the catheter assembly 130 in the first and the second directions can be repeated as needed to treat, for example, a stenosed site within a blood vessel. For example, in accordance with an exemplary embodiment, the device handle 100 can be used for the insertion of the catheter assembly 130 into a body lumen, the catheter assembly 130 including an agitator 132, arranging the agitator 132 on a distal side of a stenosed site in the body lumen, and cutting the stenosed site inside the body lumen with the agitator 132.

Figure 12:
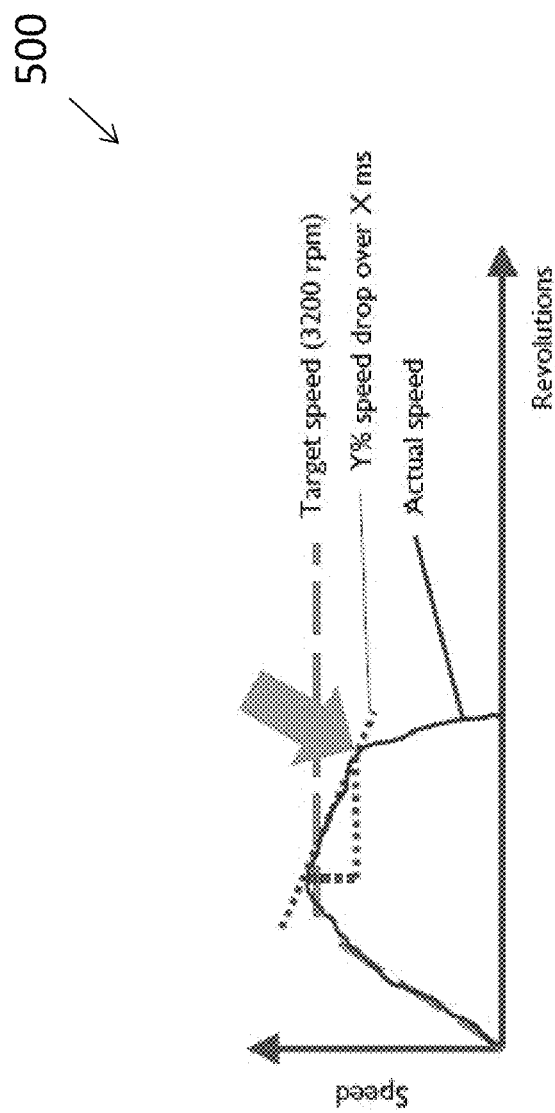
FIG. 12 is a rotational speed profile illustrating speed versus revolutions in accordance with an exemplary embodiment.
Figure 13:
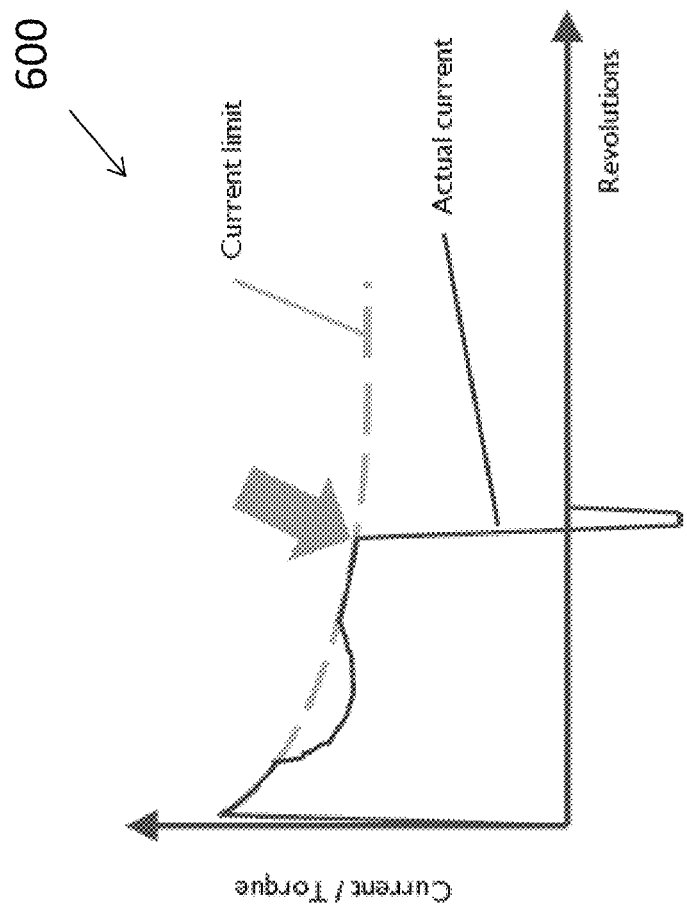
FIG. 13 is a rotational speed profile illustrating current/torque versus revolutions in accordance with an exemplary embodiment.

FIG. 12 is a rotational speed profile 500 illustrating speed versus revolutions in accordance with an exemplary embodiment, and FIG. 13 is a chart 600 illustrating current/torque versus revolutions corresponding to the speed as shown in FIG. 12. As shown in FIGS. 12 and 13, if the actual speed drops a predetermined percentage, for example, Y percentage (Y %) over X ms (X milliseconds), in accordance with an exemplary embodiment, a brake or stopping mechanism can be applied to the motor 128. For example, in accordance with an exemplary embodiment, instead of using the motor to stop or slow (i.e., brake) the agitator 132, a mechanical brake pad 920 (FIG. 16) could be used. In addition, during detection of the actual rotational speed of the catheter assembly 130, the signal received may suffer from unwanted modifications that can cause the reading to be inaccurate (i.e., noise). In accordance with an exemplary embodiment, average speed values may be used to address the unwanted modifications or noise, which may be experienced during the capture, storage, transmission, processing, or conversion of the signal corresponding to the actual rotational speed of the catheter assembly 130.

In accordance with an exemplary embodiment as shown, for example, in FIGS. 12 and 13, the device handle 100 can control the torque of a catheter assembly 130 under various rotational loads by driving the catheter assembly 130 at a target rotational speed in a first direction (for example, clockwise), detecting an actual rotational speed of the catheter assembly 130 in the first direction, comparing the target rotational speed and the actual rotational speed of the catheter assembly 130 in the first direction, and stopping the driving of the catheter assembly 130 in the first direction before a completion of predetermined number of rotations in the first direction when the actual rotational speed decreases a predetermined percentage over a predetermined time frame. In addition, as disclosed above, the process can be applied to a second direction, for example, counterclockwise.

Figure 14:
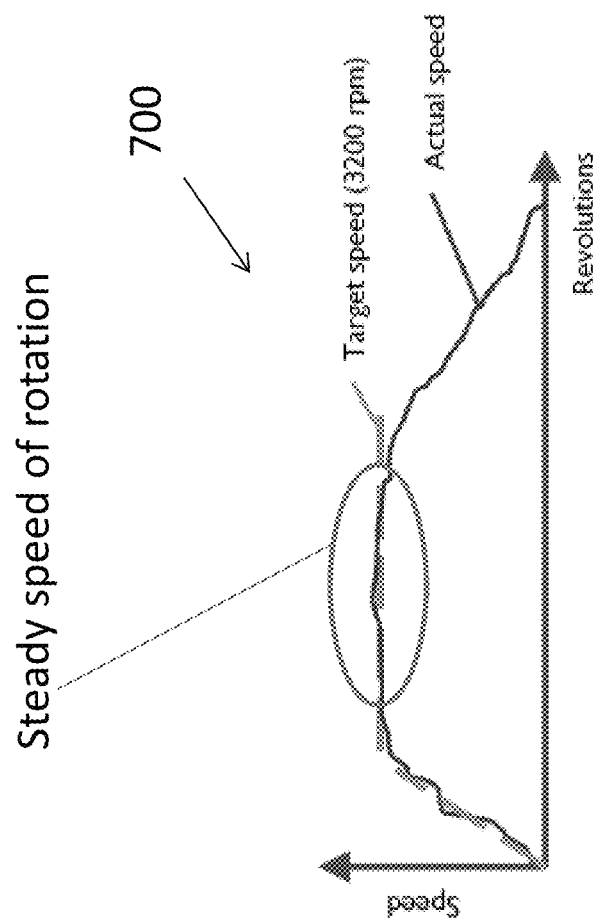
FIG. 14 is a rotational speed profile illustrating speed versus revolutions in accordance with an exemplary embodiment.
Figure 15:
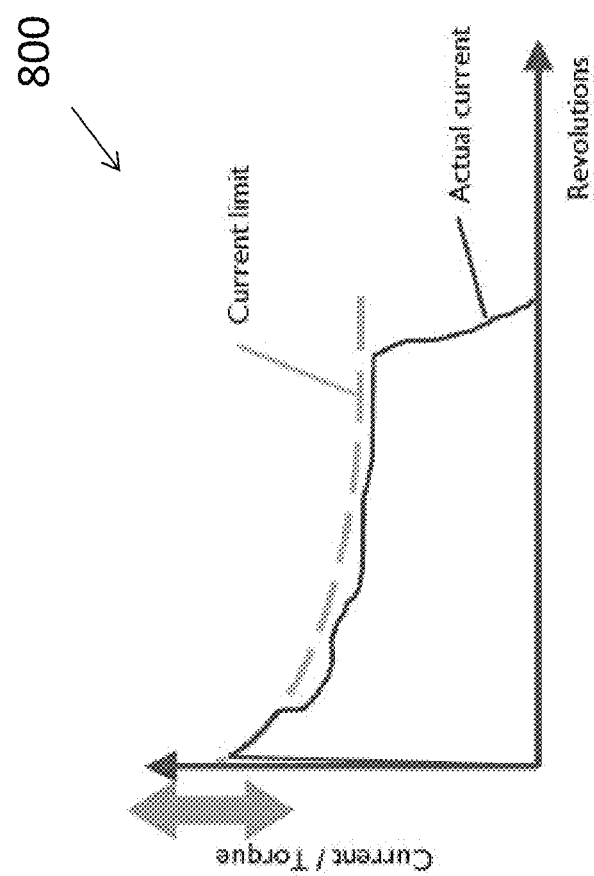
FIG. 15 is a rotational speed profile illustrating current/torque versus revolutions in accordance with an exemplary embodiment.

FIG. 14 is a rotational speed profile 700 illustrating speed versus revolutions in accordance with an exemplary embodiment, and FIG. 15 is a rotational speed profile 800 illustrating current/torque versus revolutions corresponding to the speed as shown in FIG. 15. As shown in FIGS. 14 and 15, if the actual speed matches the target speed for the cycle, no change is needed. However, if the actual speed is below target speed, the initial current limit can be increased for the next cycle.

Figure 16:
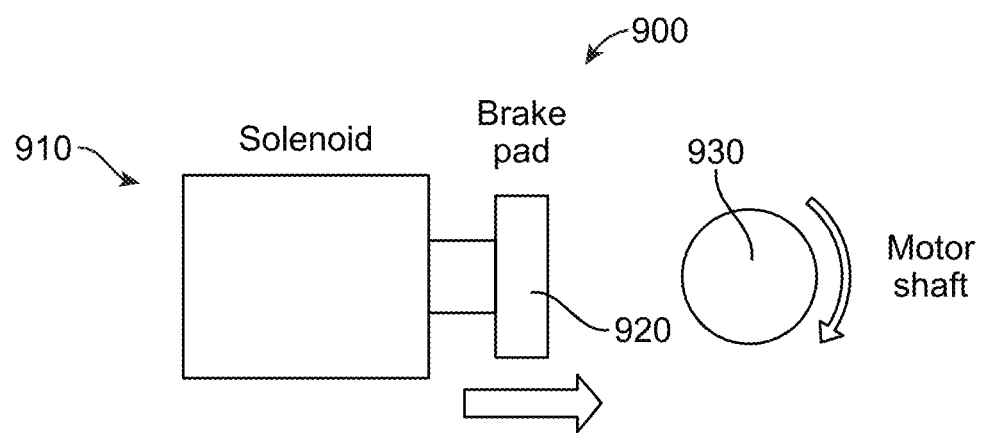
FIG. 16 is a cross-sectional view of a mechanical brake in accordance with an exemplary embodiment.

FIG. 16 is a cross-sectional view of a mechanical brake 900 in accordance with an exemplary embodiment. As shown in FIG. 16, the mechanical brake 900 can include a solenoid 910 and a brake pad 920. Upon receiving a signal from the processor, the solenoid 910 presses the brake pad 920 outward against the motor shaft 930.

Figure 17:
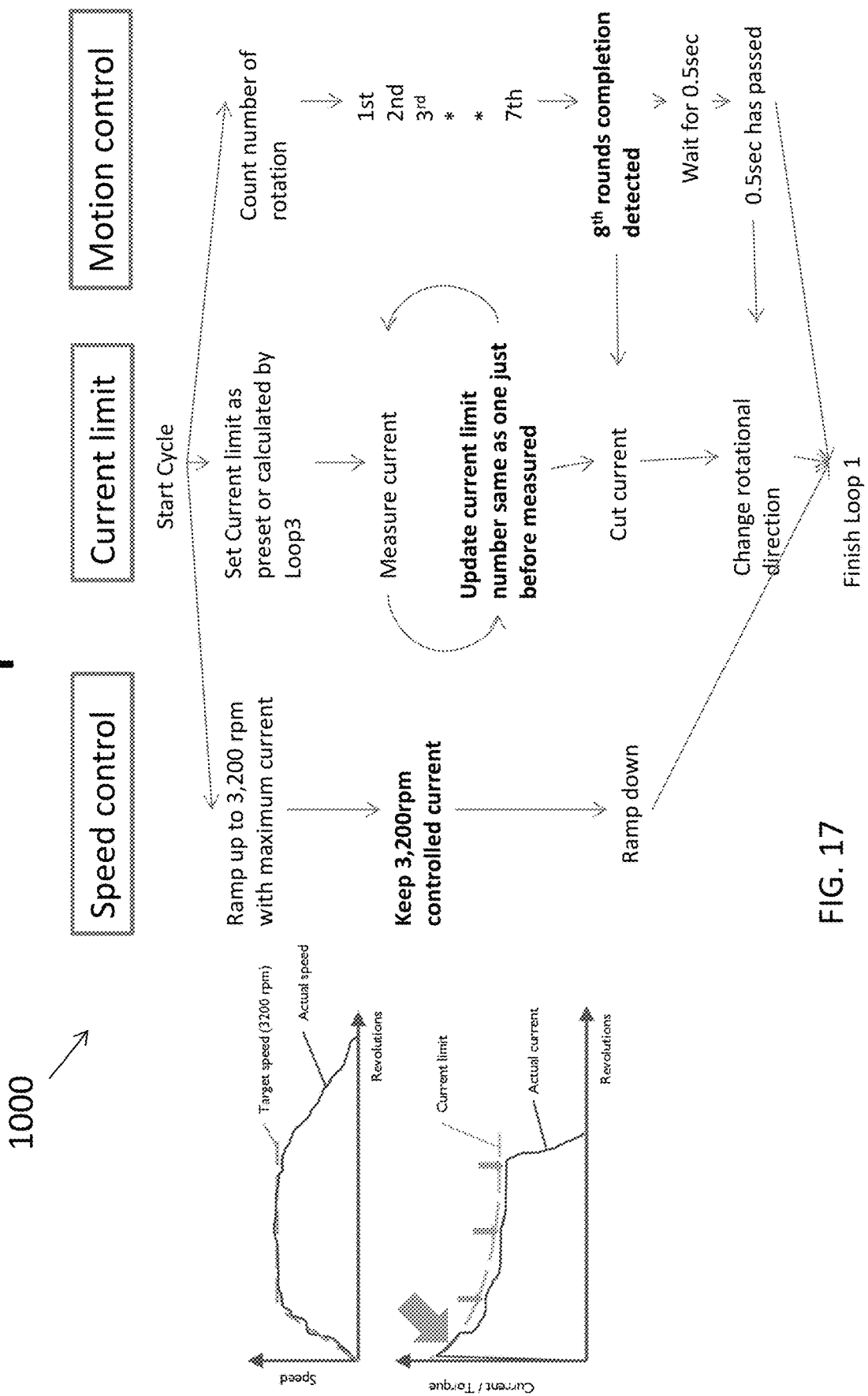
FIG. 17 is a flow chart illustrating a first loop (i.e., loop 1 or first cycle) illustrating speed control, current limit, and motion control for an exemplary system.

FIG. 17 is a flow chart illustrating a first loop (i.e., loop 1 or first cycle) 1100 illustrating speed control, current limit, and motion control for an exemplary system. As shown in FIG. 17, in the first loop 1100, the cycle includes a speed control, a current limit, and a motion control. As shown, for example in FIG. 10, during use of the handle 110 and the sliding assembly 120 to remove a blood clot, the speed 310 of the agitator 132 of the catheter assembly 130 gradually increases to a target agitator speed of, for example, approximately 3200 RPM. Once the target agitator speed is obtained, for example of 3200 RPM for a defined number of cycles, the agitator speed is then reduced or decreased (i.e., ramps down, for example, by cutting the current to the motor 120 (and agitator 132), and allowing the agitator 132 to coast to zero (0) RPM. The rotational direction of the agitator 132 is then changed (i.e., clockwise to counterclockwise or counterclockwise to clockwise). As shown in FIG. 17, for example, for a predetermine number of revolutions, for example, 8 revolutions, in the first direction (i.e., clockwise or counterclockwise) or a second direction (i.e., counterclockwise or clockwise) as disclosed herein at a target rotational speed, a portion of the 8 revolutions, i.e. at initial startup will be performed at less the target rotational speed of 3200 RPM.

Figure 19:
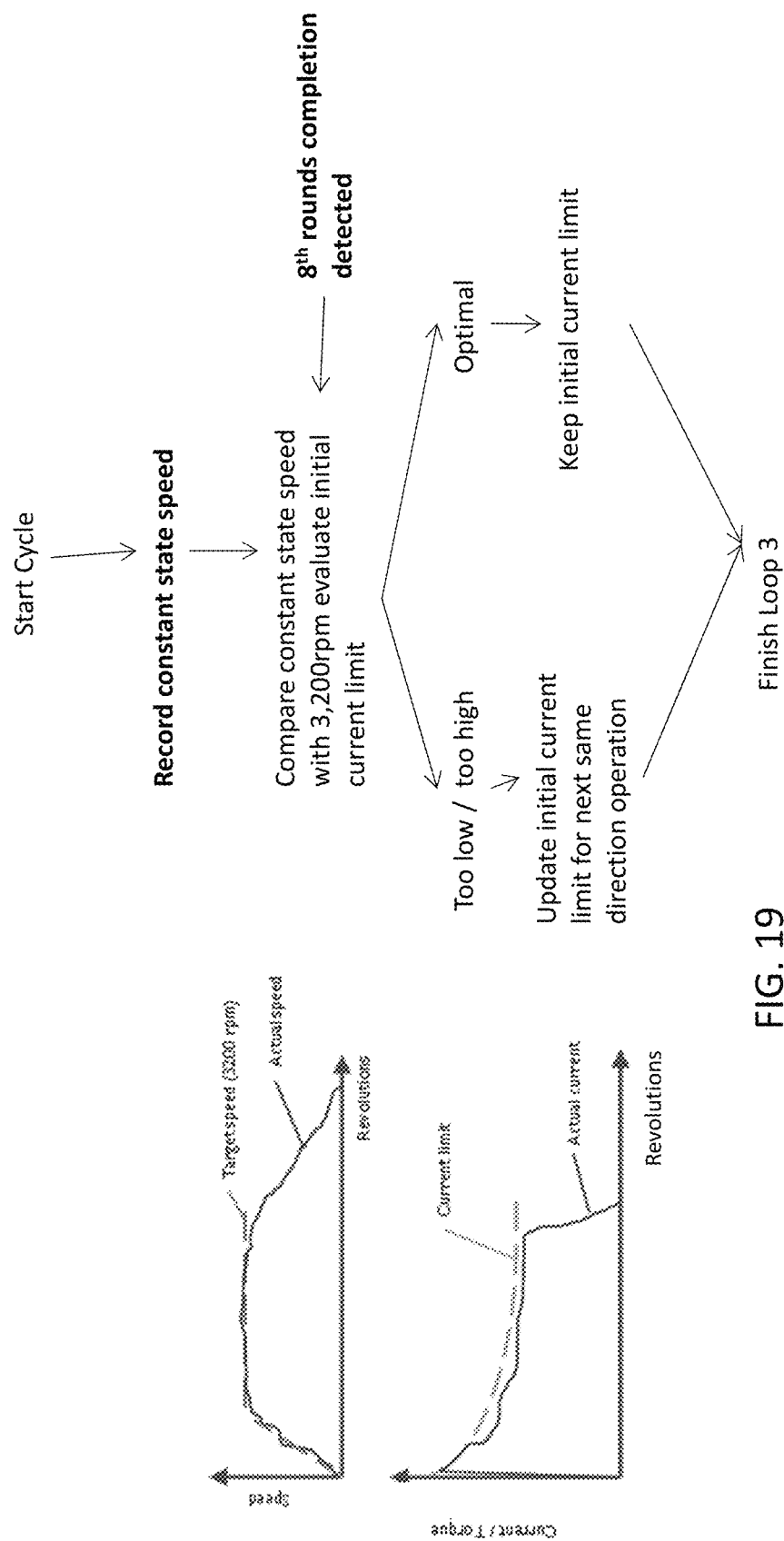
FIG. 19 is a flow chart illustrating a third loop (i.e., loop 3) for determining current limit of a motor controlling a catheter assembly of an exemplary system.

As shown in FIG. 17, for example, as shown in the rotational speed profile 400 illustrated in FIG. 11, the drive motor 128 can be controlled by the electronic components 129, for example, a processor, a microprocessor, or controller, such that the drive motor 128 follows the speed profile as shown in FIG. 10, however, the circuitry 129 does not allow the current to exceed a predetermined or predefined limit 410 as shown in FIG. 11. As shown in FIG. 17, the current limit can be preset, or alternatively calculated by loop 3 1200 (FIG. 19). The current is measured at the target rotational speed and the current limit can be updated based on measured current at the target rotational speed. The current is then cut (i.e., no longer provided) to the motor 128 driving the catheter assembly 130 and the catheter assembly 130 (i.e., agitator 132) will coast to a stop for a change in the rotational direction of the agitator. Thus, by limiting the torque, an operator of the medical device 100 can detect and stop the agitator 132 when the medical device 100 engages the blood vessel wall.

In addition, in the first loop 1000, for example, the processor can be configured to monitor (i.e., detect) the number of rotations of the agitator 132, and further carry out a process of changing the rotational direction of the catheter assembly 130 from the first direction to a second direction (for example, counterclockwise). In addition, once the predetermined number of rotations has been completed, for example, 8 revolutions, the processor can be configured to pause (i.e., completely stop the rotation) the catheter assembly 130 (and agitator 132) for a predetermined period of time, for example, 0.5 seconds, and once the predetermined period of time has elapsed, the direction of rotation of the agitator 132 can be changed completing the first loop 1000.

Figure 18:
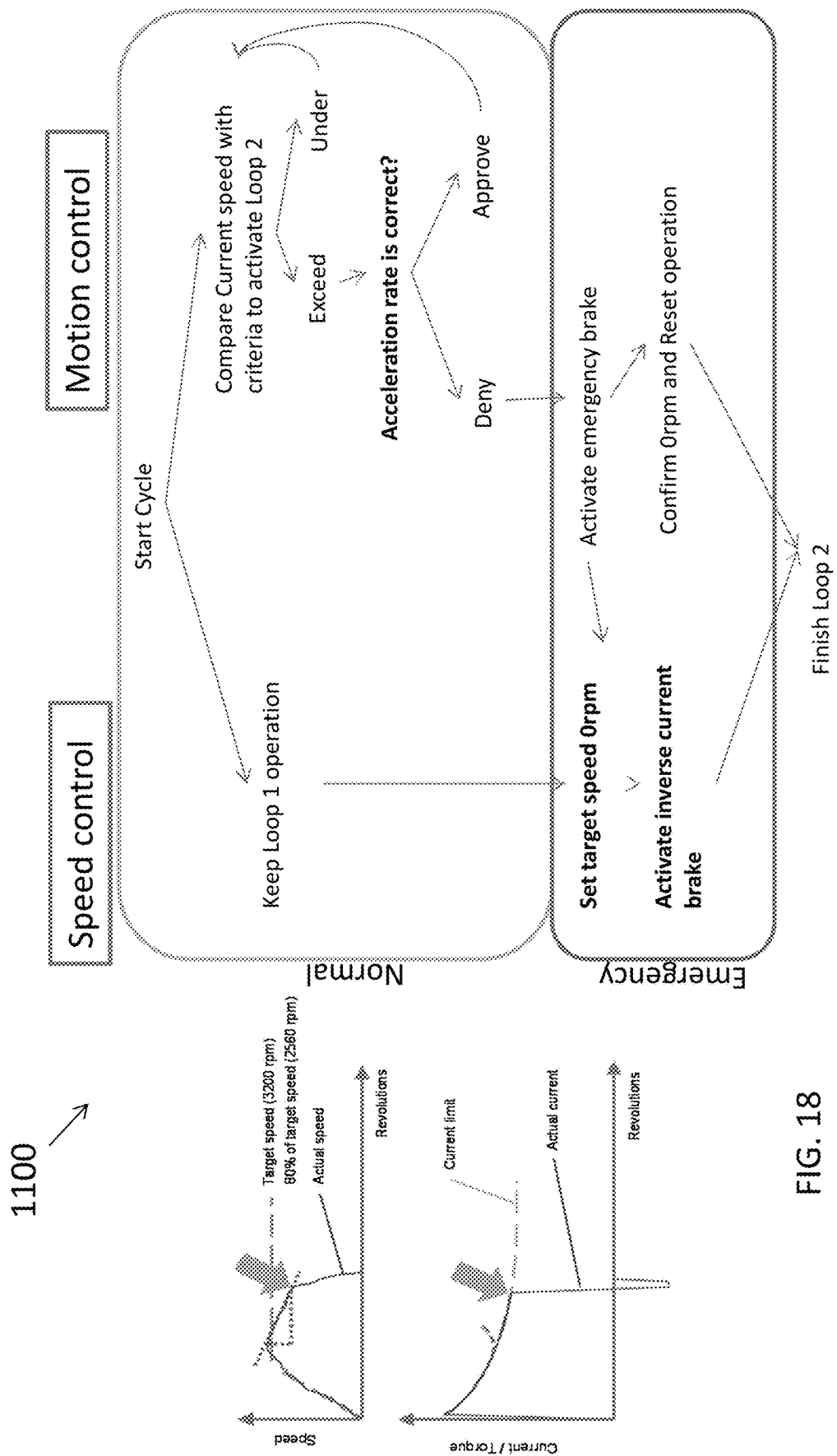
FIG. 18 is a flow chart illustrating a second loop (i.e., loop 2) illustrating speed control and motion control of an agitator of a catheter assembly of an exemplary system.

FIG. 18 is a flow chart illustrating a second loop (i.e., loop 2) 1100 illustrating speed control and motion control of the agitator 132 of the catheter assembly 130 of an exemplary system. As shown in FIG. 18, the rotational speed profile 500 as illustrated in FIG. 12 and current/torque versus revolutions as illustrated in FIG. 13 corresponding to the speed as shown in FIG. 12 can be used to control the speed and current supplied to the agitator 132. For example, at the start of a subsequent loop (for example, a second loop (i.e., loop 2), the speed (i.e., detected speed) of the agitator 132 can be compared with a predetermined target to determine if the rotational speed of the agitator 132 is exceeding the predetermined target speed, or operating at a reduced speed (i.e., under or less than the predetermined target speed). For example, if the rotational speed is within a range of the predetermined target speed (i.e., RPM), the current being providing to the motor 128 driving the catheter assembly 130 and the agitator 132 can be approved and no changes are needed.

Alternatively, as shown in FIGS. 12, 13, and 18, if the actual speed of the catheter assembly 130 and the agitator 132 drops a predetermined percentage, for example, Y percentage (Y%) over X ms (X milliseconds), an emergency situation may arise, such that a brake or stopping mechanism can be applied to the motor 128, for example, an inverse current brake. For example, in accordance with an exemplary embodiment, instead of using the motor to stop or slow (i.e., brake) the agitator 132, a mechanical brake pad 920 (FIG. 16) could be used. In addition, during detection of the actual rotational speed of the agitator 132 of the catheter assembly 130, the signal received may suffer from unwanted modifications that can cause the reading to be inaccurate (i.e., noise). In accordance with an exemplary embodiment, average speed values may be used to address the unwanted modifications or noise, which may be experienced during the capture, storage, transmission, processing, or conversion of the signal corresponding to the actual rotational speed of the catheter assembly 130. If the emergency brake is activated, for example, the speed of the agitator is preferably confirmed to be zero (0) RPM and the operation is reset, i.e., for example, as shown in the first loop 1000.

FIG. 19 is a flow chart illustrating a third loop (i.e., loop 3) 1200 for determining current limit of a motor 128 of a catheter assembly 130 of an exemplary system. As shown in FIG. 19, the cycle is started and if a constant state speed (i.e., RPM) is recorded or detected, the constant state speed is compared to the predetermined target speed, for example, 3200 RPM, and the initial current limit can be evaluated, for example, over the detected 8 revolutions. If the actual speed, for example, matches the target speed for the cycle, no change is needed to the current provided to the motor 128 and the initial current limit can be maintained or kept the same. However, if the actual speed is below the target speed (i.e., too low), or alternatively, greater than the target speed (i.e., too high) the initial current limit of the motor 128 can be increased or decreased for the next cycle. In accordance with an exemplary embodiment, the change in the current limit can be for the next cycle in a same rotational direction as the detect speed, or alternatively, the change in the current limit can be for the next rotation in a different rotational direction.

Figure 20:
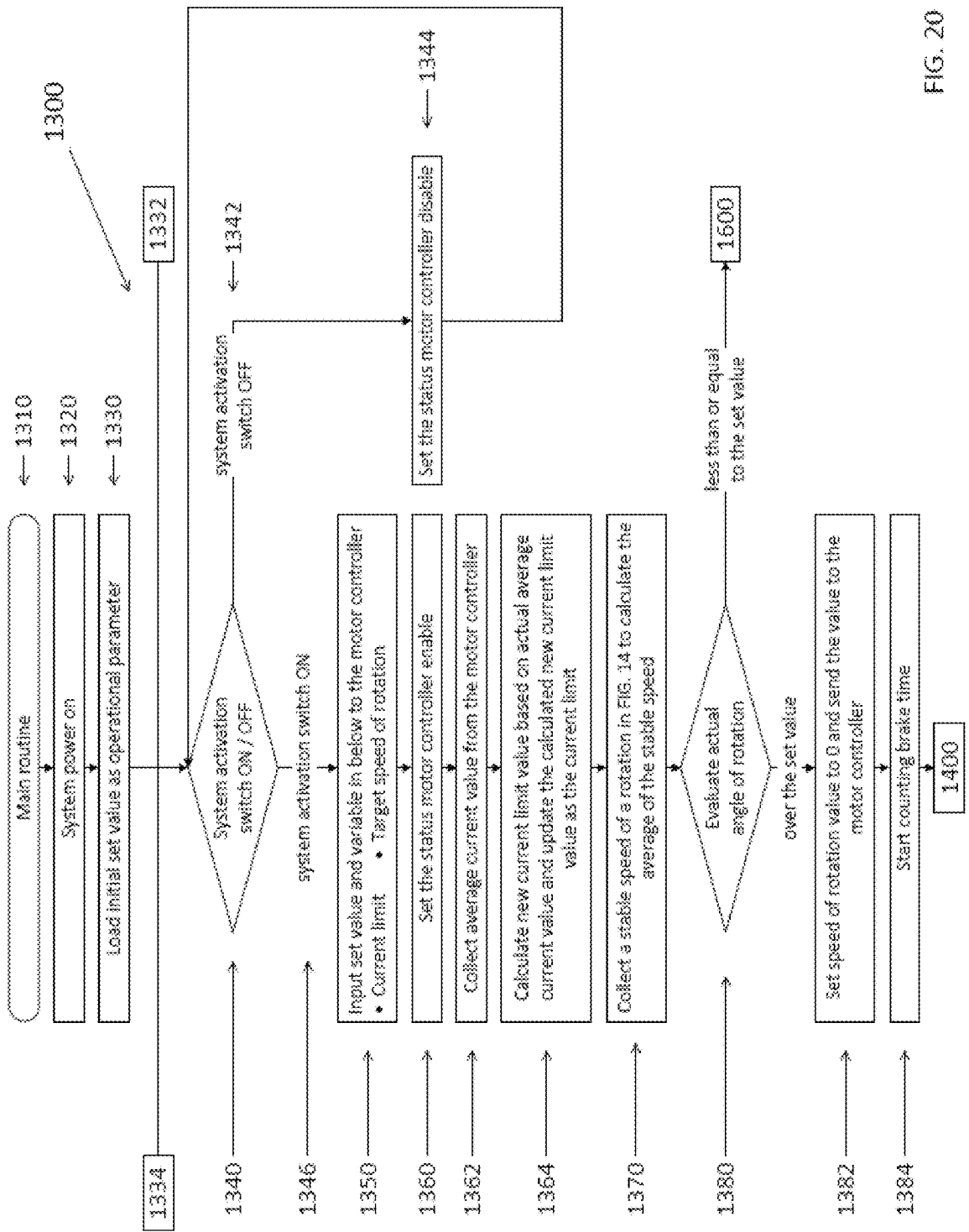
FIG. 20 is a flow chart illustrating a routine for speed control, current limit, and motion control of an agitator of a catheter assembly of an exemplary system.

FIG. 20 is a flow chart 1300 illustrating a process 1310 for speed control, current limit, and motion control of an agitator of a catheter assembly of an exemplary system in accordance with an exemplary embodiment. As shown in FIG. 20, initially, in step 1320, the system is powered "ON". Once the system is powered "ON" in step 1320, in step 1330, an initial set of values of operational parameters (i.e., predetermined values and predetermined operating conditions), for example, on the controller or microcontroller (i.e., the processor or the microprocessor, and/or one or more memories or memory cards). In accordance with an exemplary embodiment, the initial values and operating parameters can include a set constant set values, which can include target angle of rotation, speed of rotation criterial for Loop 2 1100 (i.e., speed control and motion control of the agitator 132 of the catheter assembly 130), brake time, and speed profile. In addition, variables parameters, are initially set values, which are stored in the controller (or microcontroller) and updated each cycle, which can include current limit and direction of rotation, for example, of the agitator. In step 1340, a determination is made, if the activation switch of the system is set to either "ON" or "OFF". In step 1342, if the system activation switch is in the "OFF" position, the process continues to step 1344 which sets the motor control status to "disabled" and the process returns to step 1340 until the system activation switch is changed to "ON".

Figure 23:
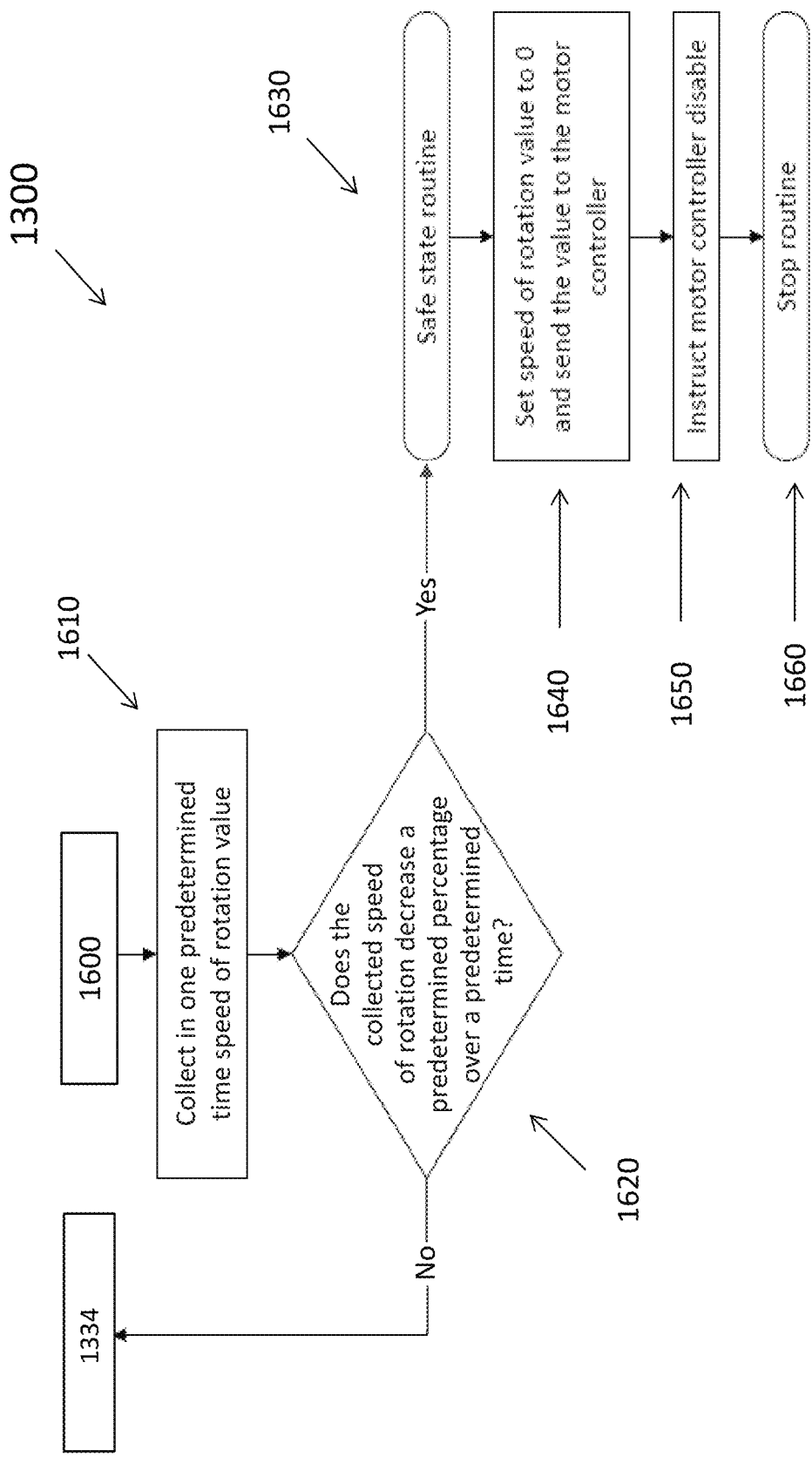
FIG. 23 is a continuation of the flow chart illustrating the routine for speed control, current limit, and motion control of the agitator of the catheter assembly of the exemplary system of FIG. 20 in accordance with an exemplary embodiment.

If the system activation switch is changed to "ON", in step 1346, the process continues to step 1350 wherein predetermined or set values and variables for the motor controller for current limit and target speed of rotation are input into the controller. In step 1360, after setting the values and variables for the motor controller, the motor controller status is set or changed to "enabled". In step 1362, the average current value from the motor controller is collected. In step 1364, a new current limit value is calculated based on the actual average current value and the controller is updated with the calculated new current limit value as the current limit. The calculated new current limit is lower than the previous current limit. A new current limit value may be calculated based on the current value that is not averaged, for example, raw current data that monitored by the motor controller before calculating the average. In step 1370, upon operation of the catheter assembly, a stable speed of the rotation of the system by (i.e., processor and/or memory and speed sensor) of the system is collected. In step 1380, an actual angle of rotation is evaluated (i.e., calculated) and if the actual angle of rotation is equal to or less than a set value (i.e., predetermined value), the process continues to step 1600 as shown in FIG. 23.

Alternatively, if the actual angle of rotation as calculated in step 1380 is greater than the set value (or predetermined value), the process continues to step 1382. In step 1382, the speed of rotation value is set to zero (0) and the value is sent to the motor controller. The process then continues to step 1384, wherein the determination of the brake time is started and the process continues to step 1400 as shown in FIG. 21.

Figure 21:
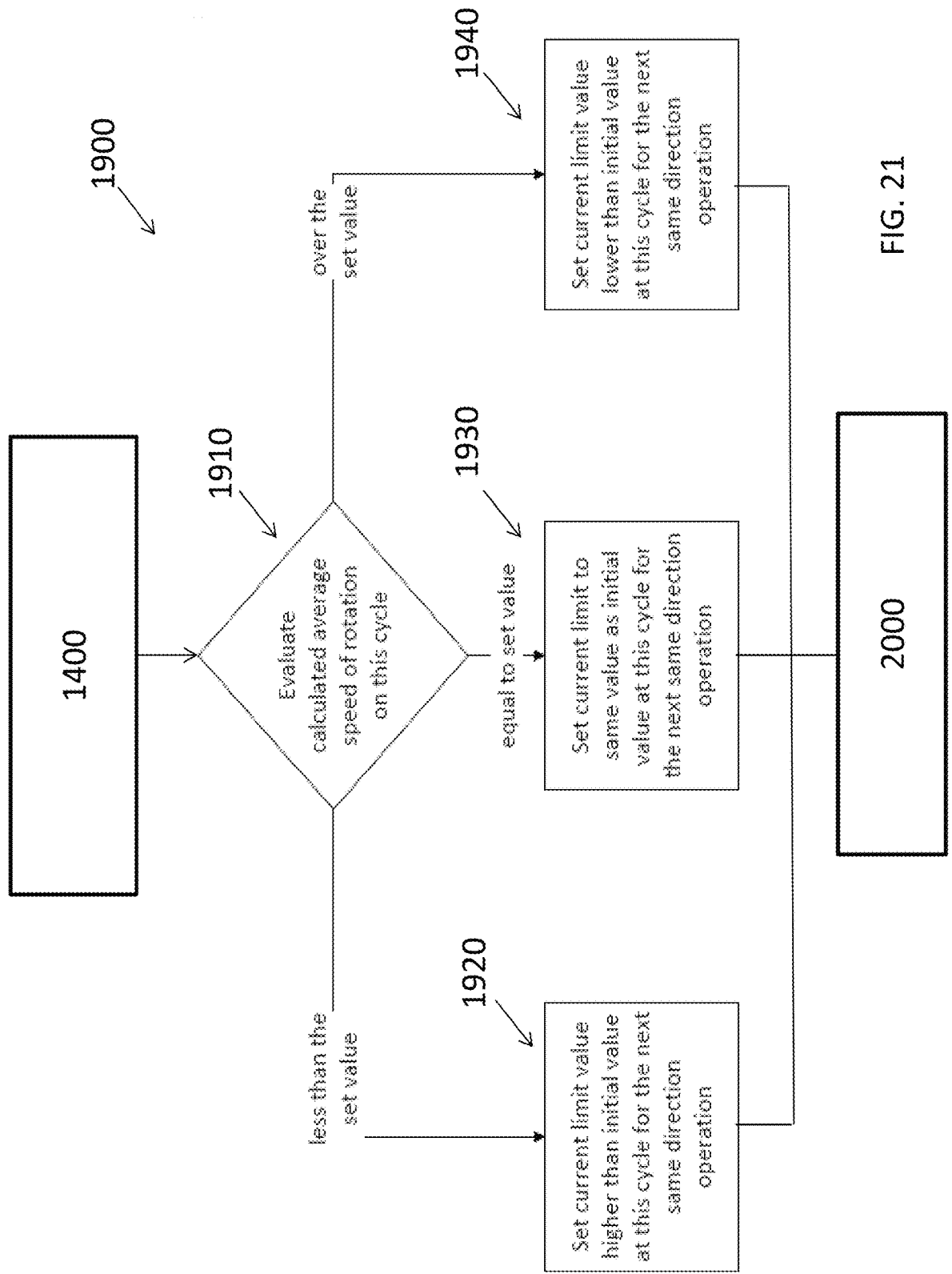
FIG. 21 is a continuation of the flow chart illustrating the routine for speed control, current limit, and motion control of the agitator of the catheter assembly of the exemplary system of FIG. 20 in accordance with an exemplary embodiment.

FIG. 21 is a flow chart 1900 illustrating for evaluating calculated average speed of rotation for a cycle of an agitator of a catheter assembly in accordance with an exemplary embodiment, for example, as shown in Loop 3 (1200). As shown in FIG. 21, the process starts at step 1910 where the average speed of rotation for a cycle is calculated. In step 1920, if the average speed is less than the set value, the current limit value is set higher than the initial value of this cycle for the next same direction operation. In step 1930, if the average speed is equal to the set value, the current limit value is set to the same value as the initial value for the next same direction operation. In step 1940, if the average speed is greater than the set value, the current limit value is set lower than the initial value of this cycle for the next same direction operation. After each of steps 1920, 1930, and 1940, the direction of rotation, for example, of the agitator, is reversed, or set in an opposite direction as shown, for example, in step 1410 of FIG. 22.

Figure 22:
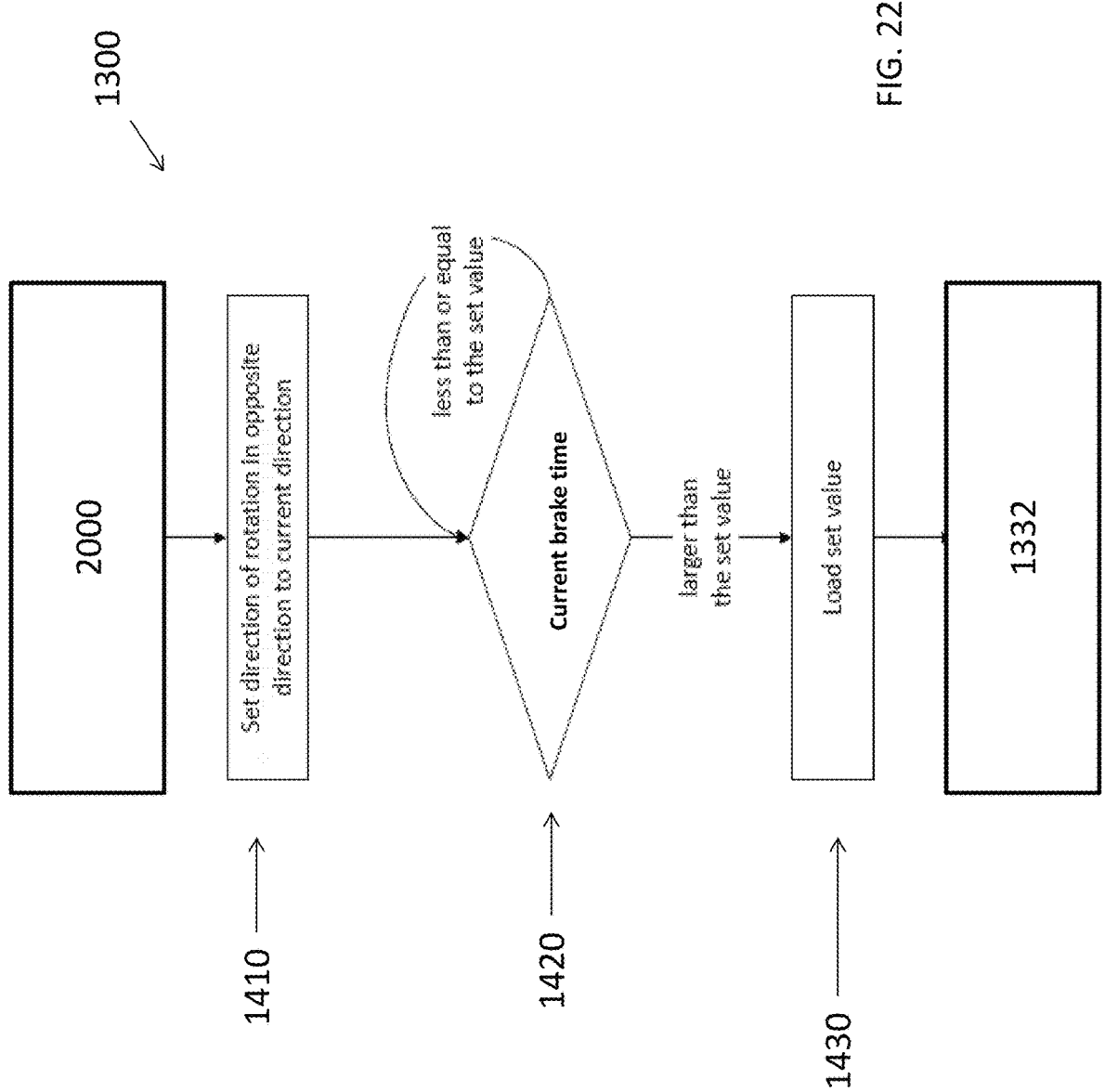
FIG. 22 is a continuation of the flow chart illustrating the routine for speed control, current limit, and motion control of the agitator of the catheter assembly of the exemplary system of FIG. 20 in accordance with an exemplary embodiment.

FIG. 22 is a continuation of the flow chart 1300 illustrating the routine for speed control, current limit, and motion control of the agitator of the catheter assembly of the exemplary system of FIG. 20. As shown in FIG. 22, in step 1410, the controller sets the direction of rotation in a direction opposite to current direction. In step 1420, current brake time is calculated. In step 1420, if the brake time is less than or equal to the set time than the brake time is recalculated. If the brake time is greater than the set value, the process continues to step 1430, where the load value is set and the process continues to step 1332 and returns to step 1340 for determination if the activation switch of the system is "ON" or "OFF" of FIG. 20.

FIG. 23 is a continuation of the flow chart 1600 illustrating the routine for speed control, current limit, and motion control of the agitator of the catheter assembly of the exemplary system of FIG. 20. As shown in FIG. 23, in step 1610, a rotational speed value for the system (i.e., speed of rotation value) is collected in one predetermined time. In step 1620, a determination is made if the collected speed of rotation decreases a predetermined percentage over a predetermined time. If the collected speed of rotation in step 1620 has not decreased a predetermined percentage over the predetermined time, the process continues to step 1334. However, if the collected speed of rotation in step 1620 has decreased a predetermined percentage over the predetermined time, the process continues to step 1630 in which a safe state routine is performed. In step 1640, the speed of rotation value is set to zero (0), and the value is sent to the motor controller. In step 1650, the motor controller is instructed to enter into a disabled state. In step 1660, the motor controller enters the disabled state and the routine is stopped A second current limit is not calculated but may be predetermined. A predetermined second current limit may be a value stored in a memory or an electronic circuit. The second current limit is information for controlling a power source such as a motor drive gear and a DC/DC converter. A processor or a physically wired circuit generates and transmits (instructs) a signal to be transmitted to the motor drive gear or the power source by using the information of the second current limit. Thus, an upper limit current which can supply electricity to the motor drive gear or the power source is determined. The circuit may be incorporated with a circuit designed for generating a specific signal indicating information (the second current limit). The signal, for example, is a pulsed signal, or an analog signal obtained by using a voltage change (from 0 V to 5 V). The second current limit is enabled when a value for monitoring a rotation state by such as a timer and a counter function is under a certain condition. Thus, the current limit is moved from a first current limit to the second current limit. Further, in a case of the first current limit, so as to transmit the upper limit current to a motor drive gear or a power source, a processor or a circuit generates a pulsed signal based on the first current limit or an analog signal obtained by using a voltage change, for example, from 0 V to 5 V. Then, the processor or the circuit can transmit (instruct) the signal to the motor drive gear or the power source.

Also, a current limit for a rotation in a first direction (for example, clockwise) and a current limit for a rotation in a second direction (for example, counterclockwise) may be provided separately.

A shaft body of a catheter assembly is formed with spiral cuts on a stainless pipe so as to improve flexibility. This spiral is a complicated shape but is winding with a deflection in one direction macroscopically. Therefore, a durability for twisting fracture of the catheter assembly is different between a first direction and a second direction. The durability for twisting fracture of the catheter assembly has relatively high strength toward a direction that the spiral is tightened, and has relatively low strength toward a direction that the spiral is opened or unwound. Thus, corresponding to the difference between the strengths obtained by the directions, a current limit for a rotation in the first direction and a current limit for a rotation in the second direction may be provided independently.

In the same way, a Nitinol (Ni—Ti) cage arranged on a distal point of a catheter assembly also is winding spirally with a deflection in one direction macroscopically. Therefore, the cage can spin with small power toward a direction that a spiral is tightened, but needs large power toward a direction that the spiral is opened. Therefore, by matching a shaft body of the catheter assembly and the cage so as to match the direction of a rotation of a low strength shaft and the direction that becomes a low resistance rotation of the cage, a maximum torque (current limit) may be set to be small. Further, by matching the direction of a rotation of a high strength shaft and the direction that becomes a high resistance rotation of the cage, the maximum torque (current limit) may be set to be large.

As an example that a second current limit is predetermined, the second current limit may be updated only once. For example, when a motor for 6 V is driven by a voltage of 12 V, a current at first to third revolutions rotating at 0 to 2000 RPM is controlled at a first current limit set to be 2 to 3 A. At this point, a twist angle of a catheter assembly keeps increasing. Then, a current at fourth to eighth revolutions rotating at 2000 to 3000 RPM is controlled at a second current limit set in advance at 1 to 2 A. At this point, a twist angle of the catheter assembly that is rotation-driven reaches a steady state (a state where torque and twist angle are balanced) at any one of fourth to eighth revolutions. The twist angle reaches the steady state and the catheter assembly, having a certain twist angle, rotates substantially without twists any more. Thus, easily a force applied to a distal point of the catheter assembly is transmitted directly to a motor. Further, the second current limit is lower than the first current limit. Therefore, for example, if the first current limit is 2 A, the second current limit is below 2 A.

As another example that a current limit to be updated is determined, the current limit may be updated twice or more. The current limit is updated, for example, three times. For example, when a motor for 6 V is driven by a voltage of 12 V, a current at first revolution rotating at 0 to 500 RPM is controlled at a first current limit set to be 2 to 3 A. At this point, a twist angle of a catheter assembly keeps increasing. Then, a current at second to third revolutions rotating at 500 to 2000 RPM is controlled at a second current limit set in advance at 1 to 2 A. The second current limit is lower than the first current limit. At this point, the twist angle of the catheter assembly keeps increasing. Then, a current at fourth to sixth revolutions rotating at 2000 to 3000 RPM is controlled at a third current limit set in advance at 1 to 2 A. Further, the third current limit is lower than the second current limit. The twist angle of the catheter assembly reaches the steady state at any one of fourth to sixth revolutions. Then, a current at seventh to eighth revolutions rotating at 3000 RPM is controlled at a fourth current limit set in advance at 0.5 to 2 A. Further, the fourth current limit is lower than the third current limit. The twist angle of the catheter assembly reaches the steady state at any one of seventh to eighth revolutions.

The detailed description above describes a device handle for a medical device and treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for controlling, by a processor, rotational speed of a catheter assembly under various rotational loads, the method comprising:
   actuating, by the processor, the catheter assembly to rotate in alternating cycles of rotation in a first direction and cycles of rotation in a second direction opposite to the first direction according to a first current limit stored in the processor, the first current limit being an upper limit of a motor current that applies a rotational force to the catheter assembly;
   calculating, by the processor, a current value of the motor current within a rotational period of the first current limit; and
   updating, by the processor, the upper limit of the motor current from the first current limit to a second current limit when a cycle of rotation of the catheter assembly switches.

2. The method of claim 1, comprising:
   monitoring and collecting, by the processor, the current value within a rotational period of the first current limit; and
   calculating, by the processor, the second current limit based on the current value collected within the rotational period of the first current limit.

3. The method of claim 2, comprising:
   calculating, by the processor, the second current limit based on an average current value within the rotational period of the first current limit.

4. The method of claim 3, wherein the rotational period of the second current limit is a series of rotational periods of the first current limit.

5. The method of claim 1, wherein the second current limit is a predetermined value that is stored in the processor.

6. The method of claim 1, comprising:
   calculating, by the processor, the second current limit based on an average current value within the rotational period in which the first current limit is applied;
   updating, by the processor, a third current limit calculated based on the current value within a rotational period in which the second current limit is applied; and
   wherein the third current limit is lower than the first current limit and the second current limit.

7. The method of claim 1, wherein the second current limit is lower than the first current limit.

8. The method of claim 7, comprising:
   updating, by the processor, a current limit, which is an upper limit of a motor current of the motor, from the second current limit to a third current limit calculated based on the current value within a rotational period from the second current limit; and
   the third current limit is lower than the first current limit and the second current limit.

9. A method of limiting torque of a catheter assembly with a rotational profile, the method comprising:
   actuating, by the processor, the catheter to rotate in alternating cycles of rotation in a first direction and cycles of rotation in a second direction opposite to the first direction according to a starting value for a current limit of a motor, the current limit being an upper limit of a motor current that applies a rotational force to the catheter assembly, and wherein the motor is configured to drive the catheter assembly;
   calculating, by the processor, a motor current of the motor during a driving of the catheter assembly in the first direction; and
   updating, by the processor, the current limit of the motor as a function of the current limit based on the calculated motor current.

10. The method of claim 9, wherein the setting of the starting value for the current limit of the motor includes setting the starting value for the current limit of the motor to a preset limit when the catheter assembly is first activated.

11. The method of claim 9, wherein after the catheter assembly completes the rotational profile, the method further comprising:
   gradually decreasing, by the processor, the updated current limit of the motor.

12. The method of claim 9, wherein the updating of the current limit of the motor includes updating the current limit of the motor after a predetermined number of rotations of the catheter assembly.

13. The method of claim 12, wherein the updating of the current limit of the motor includes updating the current limit of the motor to an updated current limit after a first predetermined number of rotations of the catheter assembly, and further comprising further updating the current limit of the motor to a further updated current limit after a second predetermined number of rotations of the catheter assembly.

14. The method of claim 13, wherein the further updating of the current limit of the motor to the further updated current limit includes further updating the current limit of the motor to the updated current limit that is less than the updated current limit.

15. The method of claim 13, wherein the updating of the current limit of the motor to the updated current limit includes updating the current limit of the motor to the updated current limit that is less than the starting value for the current limit of the motor.

16. A device handle for cutting substances inside a body lumen, the device handle comprising:
a slide assembly, the slide assembly including a drive shaft assembly configured to rotate a catheter assembly, a motor configured to impart a rotational force to the drive shaft assembly and the catheter assembly, and a processor,
the processor being configured to:
rotatably drive the catheter assembly to reach a target rotational speed in a first direction;
update a current limit, which is an upper limit of a motor current of the motor, from a first current limit in the first direction to a second current limit in the first direction, the second current limit being lower than the first current limit in the first direction;
if a rotational speed in the first direction is not achieved at the target rotational speed, setting a first current limit in the second direction higher than the first current limit in the first direction when driving the catheter assembly such that the catheter assembly reaches the target rotational speed in the second direction; and
alternate the rotatable driving of the catheter assembly between the first direction and the second direction.

17. The device handle of claim 16, wherein if the rotational speed in the first direction exceeds the target rotational speed, setting the first current limit in the second direction that is lower than the first current limit in the first direction when drive the catheter assembly so that the catheter assembly attains the target rotational speed in the second direction.

18. The device handle of claim 16, wherein if the rotational speed in the first direction is achieved, setting the first current limit in the second direction that is the same as the first current limit in the first direction when drive the catheter assembly so that the catheter assembly attains the target rotational speed in the second direction.

19. The device handle of claim 16, wherein the processor is configured to:
monitor the current value in rotational periods of the first current limit; and
calculate the second current limit based on the current value collected in the rotational periods of the first current limit.

20. The device handle of claim 16, wherein the processor is configured to set the second current limit to a predetermined value.

* * * * *